United States Patent
Schmaus et al.

(10) Patent No.: US 7,582,681 B2
(45) Date of Patent: *Sep. 1, 2009

(54) SYNERGISTIC MIXTURES OF 1,2-ALKANE DIOLS

(75) Inventors: Gerhard Schmaus, Hoexter-Bosseborn (DE); Sabine Lange, Holzminden (DE); Holger Joppe, Dassel (DE)

(73) Assignee: Symrise GmbH & Co. KG, Holzminden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/502,132

(22) PCT Filed: Oct. 17, 2002

(86) PCT No.: PCT/EP02/11611

§ 371 (c)(1),
(2), (4) Date: Jul. 20, 2004

(87) PCT Pub. No.: WO03/069994

PCT Pub. Date: Aug. 28, 2003

(65) Prior Publication Data

US 2005/0222276 A1 Oct. 6, 2005

(30) Foreign Application Priority Data

Feb. 19, 2002 (DE) ................. 102 06 759

(51) Int. Cl.
*A01N 31/00* (2006.01)
*A61K 31/045* (2006.01)
*A61K 9/12* (2006.01)

(52) U.S. Cl. .................. 514/738; 514/724; 424/44
(58) Field of Classification Search .................. 424/44; 514/564, 724
See application file for complete search history.

(56) References Cited

U.S. PATENT DOCUMENTS 5,670,160 A * 9/1997 Eggensperger et al. ...... 424/405
6,123,953 A 9/2000 Greff
2001/0036964 A1* 11/2001 Clarkson et al. ............. 514/564
2002/0098211 A1* 7/2002 Cupferman et al. ......... 424/401
2003/0100613 A1* 5/2003 Riebel et al. ................ 514/609

FOREIGN PATENT DOCUMENTS

| DE | 2204943 | 2/1972 |
|---|---|---|
| DE | 22 04 943 A | 8/1973 |
| DE | 199 27 891 A | 12/2000 |
| FR | 2 747 572 A | 10/1997 |
| JP | 51-91327 | 8/1976 |
| JP | 10-194950 | 7/1998 |
| JP | 11-335258 | 12/1998 |
| JP | 11-510176 | 9/1999 |
| JP | 11-310506 | 11/1999 |
| JP | 11-322591 | 11/1999 |
| JP | 2001-514205 | 9/2001 |
| JP | 2001-278728 | 10/2001 |
| JP | 2002-3331 | 1/2002 |
| JP | 2002003330 | 1/2002 |
| JP | 2003-81736 | 9/2003 |
| WO | WO 00/00164 | 1/2000 |

OTHER PUBLICATIONS

Greff (FR 2 747 572, partial translation).*
Database WPI Section Ch, Week 197639 Derwent Publications Ltd., London, GB; XP002022306 & JP51091327A (Kao Soap Co Ltd), Aug. 10, 1976.
Dictionary of Cosmetic Materials, p. 383, Chuo Printing Co., Ltd., Nov. 29, 2003.

* cited by examiner

*Primary Examiner*—Yong S Chong
(74) *Attorney, Agent, or Firm*—Novak Druce+Quigg; Gregory A. Nelson; Gregroy M. Lefkowitz

(57) ABSTRACT

The use of mixtures of two, three or more straight-chain 1,2-alkanediols, the chains lengths of which (i) are different and (ii) in each case are in the range of 5 to 10 C atoms, as antimicrobial active compounds is described. Compared with the pure 1,2-alkanediols, the mixtures have a synergistically intensified action.

22 Claims, 1 Drawing Sheet

SYNERGISTIC MIXTURES OF 1,2-ALKANE DIOLS

BACKGROUND OF THE INVENTION

1. Field of the Invention

Figure 1:
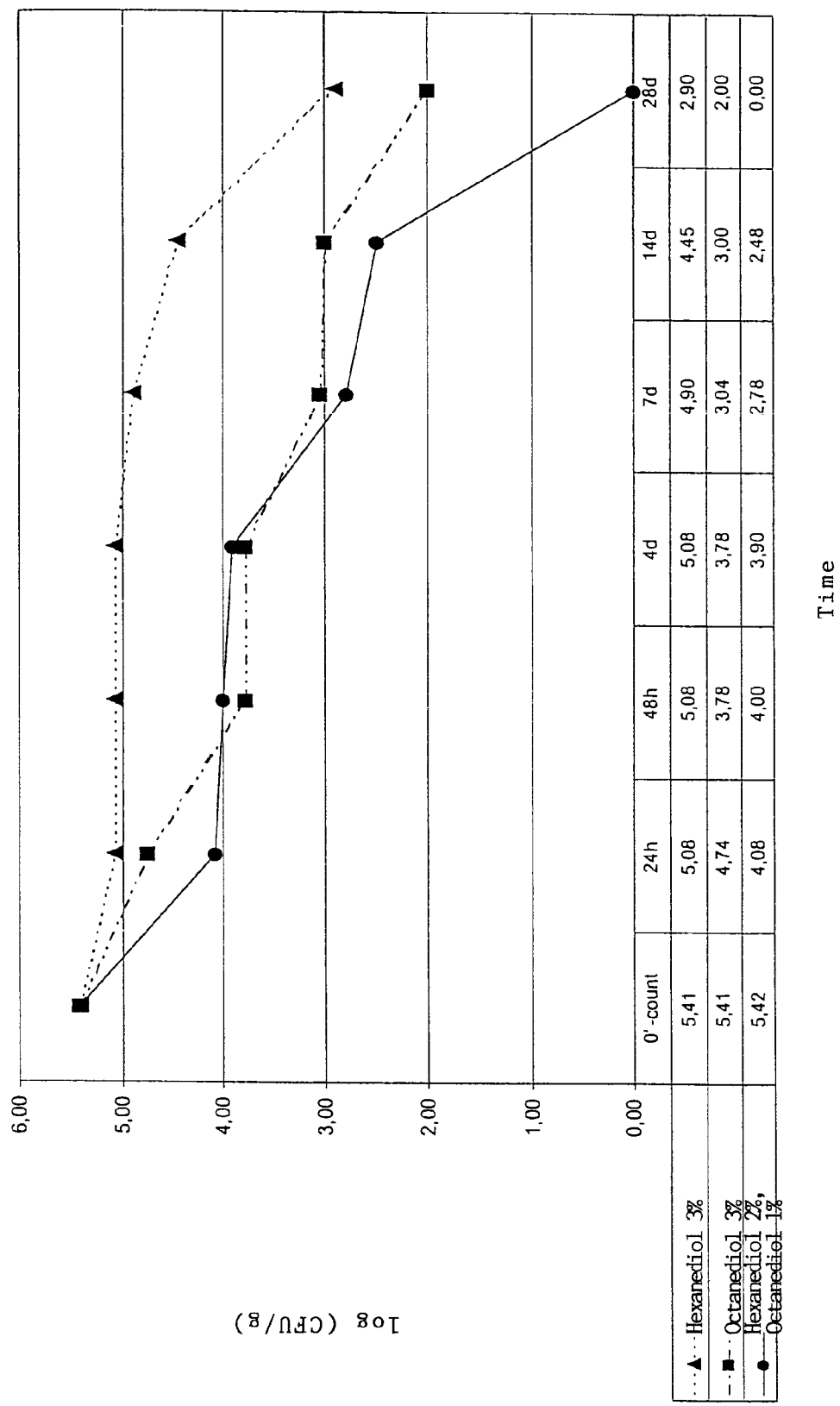

The present invention relates to the field of antimicrobial active compounds and in particular antimicrobial active compounds in which a non-branched (straight-chain) 1,2-alkanediol is present in an antimicrobially effective amount.

2. Description of the Related Art

In the cosmetic and pharmaceutical industry and also in the food industry there is an ongoing need for agents with antimicrobial properties, in particular for the preservation of products that are otherwise perishable (such as, for example, cosmetics, pharmaceutical products or foods), but also for the direct cosmetic or therapeutic treatment of microorganisms which can have an adverse influence on the human or animal body. Microorganisms that can give rise to body odour, acne, mycoses or the like may be mentioned by way of example.

It is true that a multiplicity of antimicrobial active compounds are already used in the technical fields concerned, but alternatives continue to be sought in order to be able to carry out targeted special treatments and/or reduce side effects. However, in this context when searching for alternative agents having an antimicrobial and in particular a preservative action it must be taken into account that the substances used in the cosmetic, pharmaceutical and/or food sector must be

- toxicologically acceptable,
- well tolerated by the skin,
- stable (especially in the customary cosmetic and/or pharmaceutical formulations),
- substantially and preferably completely odourless and
- able to be prepared inexpensively (i.e. using standard methods and/or starting from standard precursors).

The search for suitable (active) substances that possess one or more of the said properties to an adequate extent is made more difficult for those skilled in the art because there is no clear dependence between the chemical structure of a substance, on the one hand, and its biological activity towards specific microorganisms (germs) and its stability, on the other hand. Furthermore, there is no predictable relationship between the antimicrobial action, toxicological acceptability, tolerance by the skin and the stability of a substance.

SUMMARY OF THE INVENTION

According to a first aspect, the invention relates to mixtures of two, three or more straight-chain 1,2-alkanediols, the chain lengths of which (i) are different and (ii) in each case are in the range of 5 to 10 C-atoms. In this context the proportions of the said diols in the mixture are preferably set such that their antimicrobial action is synergistically intensified. The said 1,2-alkanediols include, in particular, 1,2-pentanediol, 1,2-hexanediol, 1,2-octanediol and 1,2-decanediol. In addition to the said 1,2-alkanediol mixtures, further (for example conventional) antimicrobial active compounds can be present, some of which—as explained further below—are able to develop a further synergistic action.

The invention is based on the surprising finding that straight-chain 1,2-alkanediols with a chain length in the range of 5 to 10 C atoms exhibit a synergistically intensified antimicrobial effect, at least against selected germs, if they are combined with a second or further straight-chain 1,2-alkanediols with chain lengths in the same range, the chain lengths of the first and the second and of the further straight-chain 1,2-alkanediols being different, however.

In particular, it has been found that the mixtures according to the invention of two, three or more straight-chain 1,2-alkanediols of different chain lengths are outstandingly suitable for use for the preservation of articles that would otherwise be perishable (see above).

Should a person skilled in the art wish to use a mixture of, for example, two straight-chain 1,2-alkanediols, the chain lengths of which (i) are different and (ii) in each case are in the range of 5 to 10 C atoms, for the antimicrobial treatment of a surface (for example of a human or animal body) or for the preservation of an article that would otherwise be perishable (for example of a cosmetic or pharmaceutical formulation), he can select a particularly suitable pairing from all conceivable pairings in the following way:

1. Determination of the straight-chain 1,2-alkanediol with a chain length in the range of 5 to 10 C atoms that has the strongest individual action.
2. Combination of the 1,2-alkanediol with the strongest individual action with each of the other straight-chain 1,2-alkanediol having a chain length in the range of 5 to 10 C atoms.
3. Determination of that combination according to 2 which has the strongest antimicrobial action.

Using the procedure outlined above, the person skilled in the art will as a rule arrive at the most effective, but always at a very good, combination of 1,2-alkanediols in the said chain length range. It is pointed out that although the alkanediol mixtures according to the invention in some cases possess a synergistically increased antimicrobial action against certain germs, against other germs, however, they only have an action that corresponds to the sum of the individual actions or is even antagonistically impaired.

Although experts in the field had already concerned themselves extensively with the antimicrobial properties of 1,2-diols, hitherto there has been no indication that mixtures of two, three or more straight-chain 1,2-alkanediols, the chain lengths of which (i) are different and (ii) in each case are in the range of 5 to 10 C atoms, possess an antimicrobial action (at least against selected germs) that is distinctly improved in the individual case. The prior art also gave no incentive to use such mixtures (combinations) as antimicrobial active compounds.

For instance, although JP 11322591 A discloses that the dosage of specific conventional antiseptic microbicides can be reduced in that a 1,2-alkanediol with, for example 5, 6 or 8 C atoms in the chain is added, it cannot be seen from this publication that a mixture of two, three or more straight-chain 1,2-alkanediols, the chain lengths of which (i) are different and (ii) in each case are in the range of 5 to 10 C atoms, constitute an antimicrobial (combination) active compound which has an extremely high activity against at least selected germs.

Quite similarly, JP 11310506 discloses a synergistic effect in the case of the combination of paraben with 1,2-pentanediol, 1,2-hexanediol or 1,2-octanediol. However, the finding of the synergistic intensification of the antimicrobial properties of the said 1,2-alkanediols, on which the present invention is based, likewise cannot be seen from JP 11310506 A.

In U.S. Pat. No. 6,123,953 certain synergistic effects between a 1,2-alkanediol having a chain length in the range of 5 to 14 carbon atoms and a glyceryl polymethacrylate gel are described. However, the US document does not disclose a combination of 1,2-alkanediols and certainly does not disclose at all such combinations (mixtures) having an antimicrobial action which is intensified compared with the action of the individual substances.

EP 0 524 548 A1 discloses specific antimicrobially active mixtures that contain, in addition to (A) an antimicrobially active aromatic alcohol of the Formula 1

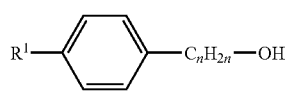

in which $R^2$ is hydrogen or an alkyl group having 1 to 4 C atoms and n is an integer from 1 to 6, (B) an antimicrobially active 1,2- or 1,3-diol of the Formula $R^2$—CHOH—$(CHR^3)_x$—$CH_2OH$, where x=0 or 1 and, if x=0, $R^2$ is an alkyl group having 6 to 22 C atoms or an alkoxymethyl or 2-hydroxyalkoxymethyl group having, in each case 6 to 22 C atoms in the alkoxy group and, if x=1, the group $R^2$ is hydrogen and $R^3$ has one of the abovementioned meanings for $R^2$, the components being in a mass ratio of 9:1 to 1:9. The antimicrobially active mixtures disclosed are said to be suitable for the preparation of antiseptically active skin cleansing agents and for the preservation of aqueous formulations of microbially degradable or perishable substances. However, it is not obvious from this technical teaching to mix two, three or more straight-chain 1,2-alkanediols, the chain lengths of which (i) are different and (ii) in each case are in the range of 5 to 10 C atoms, and to use the resulting mixture as an antimicrobial active compound. In particular, EP 0 524 548 A1 gives no indication of the possibility that such alkanediol mixtures could have a synergistically intensified antimicrobial (combination) action, so that, in particular (as possible within the framework of the present invention), the aromatic alcohols of the Formula 1 could be dispensed with.

JP 10053510 discloses combinations of pentanediol and phenoxyethanol as antiseptic agents for cosmetics.

DE 199 24 496 A1 discloses mixtures of at least one polyhydric alcohol having 5 to 15 carbon atoms (for example 1,2-pentanediol, hexanediol or octanediol) and a trialkyl citrate for combating human body odour.

Combinations of 2,4,6-cycloheptatrien-1-one-2-hydroxy-4(1-methyl-ethyl) with specific polyols are described in EP 1 000 542 A1. 1,2-octanediol, 1,2-pentanediol and/or octoxyglycerol can also be used as polyol in these combinations. However, no indication of the use of a mixture of 1,2-octanediol and 1,2-pentanediol or such a mixture of two, three or more straight-chain 1,2-alkanediols as antimicrobial active compound can be found in this publication. Rather, the function of the 1,2-alkanediols disclosed in EP 1 000 542 A1 remains unclear; in particular, from paragraph [0048] of EP 1 000 542 A1 the impression is gained that they would have only an inadequate antimicrobial activity without the presence of the said cycloheptatrienone derivative (or alternatively of a sodium capryl-lactyl-lactylate).

WO 99/56715 and WO 99/56716 relate to the use of 1,2-hexanediol as deodorant or antiperspirant. These publications as well do not disclose a synergistic intensification of the antimicrobial activity by combinations consisting of at least two diols of the general Formula 1.

In addition, a series of further documents relate to applications of 1,2-diols, but without discussing a synergistic intensification of the antimicrobial activity thereof by combinations consisting of at least two diols. To this extent, reference is made to the following documents: FR 2,755,371; WO 99/11237; WO 99/56715; JP 20 0044419; JP 11 335258; JP 10 053510; J. Food Sc. 42(3), 699-701; DE 199 24 496 und JP 20 0148720.

In view of the comprehensive research on the antimicrobial activity of individual diols having a chain length in the range of 5 to 10 C atoms it was now particularly surprising that mixtures of two, three or more straight-chain 1,2-alkanediols, the chain lengths of which (i) are difference and (ii) in each case are in the range of 5 to 10 C atoms display a strongly synergistic activity and are clearly superior to the individually dosed 1,2-diols having chain lengths in the same range in the same concentration, in particular with regard to the reduction in germ time. In particular, a CFU value (CFU=number of colony-forming units) of 0 can be achieved in the individual case only with the said mixtures according to the invention.

The use of a mixture of (a) 1,2-hexanediol and 1,2-octanediol (b) 1,2-hexanediol and 1,2-decanediol, (c) 1,2-pentanediol, 1,2-hexanediol and 1,2-octanediol, (d) 1,2-hexanediol, 1,2-octanediol and 1,2-decanediol or (e) 1,2-pentanediol, 1,2-hexanediol and 1,2-decanediol is particularly preferred. In this context see also the examples further below.

Based on the total mass of the mixture of the diols, the proportion of each individual diol should be in the range of 1 to 99% (m/m), but preferably in the range of 20 to 80% (m/m).

The 1,2-diol mixtures according to the invention are suitable not only for the preservation of perishable products such as, for example, cosmetic products, pharmaceutical products or foods, but, because of their synergistically intensified antimicrobial activity, can also be used (a) for the cosmetic treatment of microorganisms causing body odour, (b) for the cosmetic treatment of microorganisms causing acne, (c) for the cosmetic treatment of microorganisms causing mycoses and (d) for the treatment of microorganisms on or in inanimate material.

The mixtures according to the invention develop their synergistic action against a multiplicity of Gram-positive bacteria, Gram-negative bacteria, moulds and yeasts. There is a particularly good action against Gram-negative bacteria such as *Escherichia coli* and *Pseudomonas aeruginosa*, against yeasts such as *Candida albicans* and against fungi such as *Aspergillus niger*. In this context the very good activity of the 1,2-diol mixtures according to the invention against *Aspergillus niger*, a mould that can be controlled only with very great difficulty, is to be regarded as particularly advantageous, since the Applicant's own studies have shown that when individual 1,2-diols with a chain length in the range of 5 to 10 C atoms are used the CFU value thereof cannot be reduced to the value 0.

The present invention also relates to corresponding methods for the cosmetic and/or therapeutic treatment of germs and specifically, in particular, of (a) microorganisms causing body odour, (b) microorganisms causing acne and/or (c) microorganisms causing mycoses, comprising the topical application of an antimicrobially effective amount of a mixture of two, three or more straight-chain 1,2-alkanediols, the chain lengths of which (i) are different and (ii) in each case are in the range of 5 to 10 C atoms, the proportions of the said diols in the mixture being set such that their antimicrobial action is synergistically intensified.

Preferred embodiments of the method according to the invention correspond to the preferred embodiments of the use according to the invention explained above.

The human skin is populated by a multiplicity of different microorganisms which include the microorganisms already mentioned above as well as others. The majority of these microorganisms are not pathogenic and are irrelevant for the physiological condition of the skin and for its odour. Others, on the other hand, can have a decisive influence on the healthy condition of the skin. Some microorganisms which have a substantial influence on human skin flora are given in Table 1.

As the Applicant's own research now showed, the synergistically active mixtures according to the invention consisting of two, three or more straight-chain 1,2-alkanediols, the chain lengths of which (i) are different and (ii) in each case are in the range of 5 to 10 C atoms, not only have a good action against the germs already mentioned above but also against *Staphylococcus epidermidis, Brevibacterium epidermidis, Propionibacterium acnes* as well as against *Trichophyton* and *Epidermophyton* species, so that they can also be used as agents for the treatment (control) of underarm odour and foot odour and of body odour in general, as agents for the control of acne, as anti-dandruff agents and for the treatment of mycoses (in particular dermatomycoses (again see Table 1).

TABLE 1

| Microorganisms: | |
| --- | --- |
| *Staphylococcus epidermidis* | underarm odour, body odour in general |
| *Staphylococcus aureus* | atopic eczemas; wound infection |
| *Corynebacterium xerosis* | underarm odour |
| *Brevibacterium epidermidis* | underarm odour; foot odour |
| *Propionibacterium acnes* | acne |
| *Escherichia coli* | wound infection |
| *Pseudomonas aeruginosa* | wound infection |
| *Malassezia furfur* (syn. *Pityrosporum ovale*) | development of dandruff |
| *Candida albicans* | general candidoses |
| *Trichophyton mentagrophytes* | skin and nail mycoses |
| *Trichophyton rubrum* | skin and nail mycoses |
| *Epidermophyton floccosum* | skin and nail mycoses |
| *Aspergillus niger* | mould infestation |

The following supplementary remarks may be made in this context:

As a result of the bacterial degradation of substances produced in the body and contained in perspiration, such as, for example, unsaturated fatty acids, decomposition products with an unpleasant odour that can have a severe effect on bodily wellbeing are formed from precursors that have a more or less weak odour. In cosmetics, products that either suppress the formation of body perspiration (so-called antiperspirants) or substances that inhibit the growth of the bacteria of the human skin that are responsible for odour formation (deodorants) are used to prevent the formation of the substances responsible for body odour. Species of bacteria such as *Staphylococcus epidermidis, Corynebacterium xerosis* and *Brevibacterium epidermidis* generally have decisive responsibility for the formation of underarm and foot odour or body odour. In the cosmetics industry there is therefore an ongoing need for new agents for the treatment of microorganisms causing this and other body odour (including underarm and foot odour).

A microorganism that causes acne is *Propionibacterium acnes*, which is a germ that grows anaerobically. The cosmetics industry is continually looking for agents for the treatment of this germ and other microorganisms that cause acne.

All areas of the human skin can be infested by mycoses (in particular dermatomycoses and nail mycoses). Areas of the skin on which moisture and warmth can build up as a result of wearing clothing, shoes or jewellery are particularly frequently affected. Fungus diseases of the fingernail and toenail regions are experienced as being particularly unpleasant. Various species of *Trichophyton* and *Epidermophyton* frequently have decisive responsibility for the formation of mycoses. The cosmetics industry is continuously searching for novel agents for the treatment of microorganisms causing these and other mycoses.

Within the context of the present text, "treatment" is understood to be any form of influence on the microorganisms concerned by means of which the reproduction of these microorganisms is inhibited and/or the microorganisms are killed.

Preferably, the use concentration of the mixtures according to the invention consisting of two, three or more straight-chain 1,2-alkanediols, the chain lengths of which (i) are different and (ii) in each case are in the range of 5 to 10 C atoms, in the case of use as preservative in a food or as antimicrobial active compound in a cosmetic or pharmaceutical end product is in the range between 0.01 and 30% (m/m), but particularly preferentially in the range between 0.1 and 5% (m/m), in each case based on the total mass of the food or end product.

Also in a preferred method according to the invention for the cosmetic and/or therapeutic treatment of (a) microorganisms causing body odour, (b) microorganisms causing acne and/or (c) microorganisms causing mycoses, the use concentration of the synergistically active mixtures according to the invention is in the range between 0.01 and 30% (m/m) and particularly preferentially in the range between 0.1 and 5% (m/m), in each case based on the total mass of the cosmetic or pharmaceutical product which contains the mixture.

In this context the synergistically active diol mixtures can be used (a) prophylactically or (b) as needed.

The concentration of the amount of active compound that is, for example, to be applied daily is variable and depends on the physiological condition of the test person as well as on parameters specific to the individual, such as age or body weight. The synergistically active diol mixtures according to the invention can be used both on their own and also in combination with further antimicrobially active substances.

It is furthermore pointed out that in the context of the present text the terms 1,2-diol includes both the corresponding 2S-configured enantiomer and also the 2R-configured enantiomer as well as arbitrary mixtures of these 2S- and 2R-configured enantiomers. It is true that for commercial reasons it is particularly advantageous to use mixtures of racemates of the relevant diols to control microorganisms, since these are particularly easily accessible by a synthetic route; however, the pure enantiomers or non-racemic mixtures of these enantiomers are also suitable for the purposes according to the invention.

Finally, the present invention also relates to corresponding antimicrobial compositions comprising:
(a) a mixture of two, three or more straight-chain 1,2-alkanediols, the chain lengths of which (i) are different and (ii) in each case are in the range of 5 to 10 C atoms, and
(b) an excipient compatible with the said mixture, as well as antimicrobial compositions comprising:
(a) a mixture of two, three or more straight-chain 1,2-alkanediols, the chain lengths of which (i) are different and (ii) in each case are in the range of 5 to 10 C atoms, as antimicrobial active compound, and
(b) an excipient compatible with the said mixture and also, optionally,
a further antimicrobial active compound that does not comprise a straight-chain 1,2-alkanediol.

With regard to the preferred embodiments of the antimicrobial compositions according to the invention, what has been stated above applies correspondingly.

Further uses/methods and compositions according to the invention can be taken from the following explanations and the appended patent claims.

In particular insofar as they are used against germs causing body odour, compositions that contain a synergistically active mixture according to the invention are as a rule applied topically in the form of solutions, creams, lotions, gels, sprays or the like. For other purposes, an oral (tablet, capsules, powders, drops), intravenous, intraoccular, intraperitineal or intramuscular application or an application in the form of an impregnated bandage is sensible in some cases.

The synergistically active mixtures of 1,2-alkanediols used according to the invention can be incorporated without difficulty in conventional cosmetic or dermatological/keratological formulations such as, inter alia, pump sprays, aerosol sprays, creams, shampoos, ointments, tinctures, lotions, nail care products (for example nail varnishes, nail varnish removers, nail balsams) and the like. In this context it is also possible, and in some cases advantageous, to combine the synergistic mixtures of 1,2-alkanediols used according to the invention with further active compounds, for example with other substances having an antimicrobial, antimycotic and/or antiviral action. In this context the cosmetic and/or dermatological/keratological formulations containing the synergistically active 1,2-alkanediols can otherwise be of customary composition and serve for treatment of the skin and/or the hair in the sense of a dermatological or keratological treatment or of a treatment in the sense of care cosmetics. However, they can also be used in make-up products in decorative cosmetics.

If the synergistic mixtures of 1,2-alkanediols according to the invention are used as active compounds for the preservation of organic material, a further preservative, or several further preservatives, can advantageously additionally be used. Preferably, preservatives such as benzoic acid, the esters and salts thereof, propionic acid and salts thereof, salicylic acid and salts thereof, 2,4-hexanoic acid (sorbic acid) and salts thereof, formaldehyde and paraformaldehyde, 2-hydroxybiphenyl ether and salts thereof, 2-zincsulphidopyridine-N-oxide, inorganic sulphites and bisulphites, sodium iodate, chlorobutanolum, 4-ethylmercury-(II)5-amino-1,3-bis(2-hydroxy)benzoic acid, salts and esters thereof, dehydratcetic (sic) acid, formic acid, 1,6-bis(4-amidino-2-bromophenoxy)-n-hexane and salts thereof, the sodium salt of ethylmercury-(II)-thiosalicylic acid, phenylmercury and salts thereof, 10-undecylenic acid and salts thereof, 5-amino-1,3-bis(2-ethylhexyl)-5-methyl-hexahydropyrimidine, 5-bromo-5-nitro-1,3-dioxane, 2-bromo-2-nitro-1,3-propanediol, 2,4-dichlorobenzyl alcohol, N-(4-chlorophenyl)-N'-(3,4-dichlorophenyl)-urea, 4-chloro-m-cresol, 2,4,4'-trichloro-2'-hydroxy-diphenyl ether, 4-chloro-3,5-dimethylphenol, 1,1'-methylene-bis(3-(1-hydroxymethyl-2,4-dioximidazolidin-5-yl)urea), poly-(hexamethylene diguanide) hydrochloride, 2-phenoxyethanol, hexamethylentetramine, 1-(3-chloroallyl)-3,5,7-triaza-1-azonia-adamantane chloride, 1(4-chlorphenoxy)-1(1H-imidazol-1-yl)-3,3-dimethyl-2-butanone, 1,3-bis-(hydroxy-methyl)-5,5-dimethyl-2,4-imidazolidinedione, benzyl alcohol, Octopirox, 1,2-dibromo-2,4-dicyanobutane, 2,2'-methylene-bis(6-bromo-4-chloro-phenol), bromo-chlorophene, mixture of 5-chloro-2-methyl-3(2H)-isothiazolinone and 2-methyl-3(2H) isothiazolinone with magnesium chloride and magnesium nitrate, 2-benzyl-4-chlorophenol, 2-chloracetamide, chlorhexidine, chlorhexidine acetate, chlorhexidine gluconate, chlorhexidine hydrochloride, 1-phenoxy-propan-2-ol, N-alkyl ($C_{12}$-$C_{22}$) trimethyl-ammonium bromide and chloride, 4,4-dimethyl-1, 3-oxazolidine, N-hydroxymethyl-N-(1,3-di(hydroxymethyl)-2,5-dioxoimidazolidin-4-yl)-N'-hydroxy-methyl urea, 1,6-bis(4-amidino-phenoxy)-n-hexane and salts thereof, glutaraldehyde 5-ethyl-1-aza-3,7-dioxabicyclo(3.3.0)octane, 3-(4-chlorphenoxy)-1,2-propanediol, hyamine, alkyl-($C_8$-$C_{18}$)-dimethyl-benzyl-ammonium chloride, alkyl-($C_8$-$C_{18}$)-dimethyl-benzyl ammonium bromide, alkyl-($C_8$-$C_{18}$)-dimethyl-benzylammonium saccharinate, benzylhemiformal, 3-iodo-2-propinyl-butyl carbamate, or sodium hydroxymethyl-aminoacetate are preferably chosen here. The advantage of active compound combinations consisting of (a) a synergistic mixture of 1,2-alkanediols according to the invention and (b) at least one further preservative, which surprisingly can be achieved, will be explained in more detail on the basis of Example 3.

If the synergistic mixtures of 1,2-alkanediols according to the invention are to be used mainly for the inhibition of the growth of undesired microorganisms on or in animal organisms, a combination with further antibacterial or antimycotic active compounds can be advantageous in some cases here as well. Further active compounds that are worthy of mention in this regard are, in addition to the large group of conventional antibiotics, in particular the products relevant for cosmetics, such as triclosan, climbazol, octoxyglycerol, Octopirox (1-hydroxy-4-methyl-6-(2,4,4-trimethylpentyl)-2(1H)-pyridone, 2-aminoethanol), chitosan, farnesol, glycerol monolaurate or combinations of the said substances, which, inter alia, are used against underarm odour, foot odour or dandruff.

In addition, the synergistic mixtures of 1,2-alkanediols can also be used particularly advantageously in combination with perspiration-inhibiting active compounds (antiperspirants) for controlling body odour. Perspiration-inhibiting active compounds used are, in particular, aluminium salts, such as aluminium chloride, aluminium chlorohydrate, nitrate, sulphate, acetate etc. In addition, however, the use of zinc, magnesium and zirconium compounds can also be advantageous. Essentially the aluminium salts and—to a somewhat lesser extent—aluminium/zirconium salt combinations have proved their worth for use in cosmetic and dermatological antiperspirants. The partially neutralised aluminium hydroxychlorides, which are thus better tolerated by the skin but are not quite as effective, are also worthy of mention. In addition to aluminium salts, further substances can also be used, such as, for example, a) protein-precipitating substances such as, inter alia, formaldehyde, glutaraldehyde, natural and synthetic tanning agents and also trichloroacetic acid, which give rise to surface closure of the sweat glands, b) local anaesthetics (inter alia dilute solutions of, for example, lidocaine, prilocaine or mixtures of such substances) that switch off the sympathetic supply of the sweat glands by blocking the peripheral nerve paths, c) zeolites of the X, A or Y type, which in addition to reducing sweat secretion also act as adsorbents for bad odours, and d) botulinus toxin (toxin of the bacterium *Chlostridium botulinum*), which is also used in the case of hyperhidrosis, a pathologically increased sweat secretion, and the action of which is based on an irreversible blockage of the release of the transmitter substance acetylcholine relevant for sweat secretion.

If the synergistic mixtures of 1,2-alkanediols according to the invention are to be used for the antimicrobial treatment of a surface (for example of a human or animal body), a combination with (metal) chelating agents can be advantageous in some cases. In this context, (metal) chelating agents that are preferably to be used are, inter alia, α-hydroxy fatty acids, phytic acid, lactoferrin, α-hydroxy acids, such as, inter alia, citric acid, lactic acid and malic acid, as well as humic acids, bile acids, bile extracts, bilirubin, biliverdin or EDTA, EGTA and derivatives thereof.

For use, the cosmetic and/or dermatologically active synergistic mixtures of 1,2-alkanediols according to the invention are applied to the skin and/or the hair in an adequate amount in the manner customary for cosmetics and dermatological products. In this context cosmetic and dermatological formulations that contain a mixture according to the invention and additionally act as a sunscreen offer particular advantages. Advantageously, these formulations contain at least one UVA filter and/or at least one UVB filter and/or at least one inorganic pigment. In this context the formulations can be in various forms, such as are, for example, customarily employed for sunscreen formulations. Thus, they can be, for example, a solution, an emulsion of the water-in-oil (W/O) type or of the oil-in-water (O/W) type or a multiple emulsion, for example of the water-in-oil-in-water (W/O/W) type, a gel, a hydrodispersion, a solid stick or also an aerosol.

As mentioned, formulations that contain a synergistic mixture of 1,2-alkanediols can advantageously be combined with substances that absorb UV radiation, the total amount of the filter substances being, for example, 0.01% (m/m) to 40% (m/m), preferably 0.1% to 10% (m/m), in particular 1.0 to 5.0% (m/m), based on the total weight of the formulations, in order to make available cosmetic formulations that protect the hair and/or the skin against ultraviolet radiation.

If the formulations according to the invention contain UVB filter substances, these can be oil-soluble or water-soluble. Advantageous oil-soluble UVB filters are, for example: 3-benzylidenecamphor derivatives, preferably 3-(4-methylbenzylidene)camphor, 3-benzylidenecamphor; 4-aminobenzoic acid derivatives, preferably 2-ethylhexyl 4-(dimethylamino)-benzoate, amyl 4-(dimethylamino)benzoate, esters of cinnamic 1 preferably 2-ethylhexyl 4-methoxycinnamate, isopentyl 4-methoxycinnamate; esters of salicylic acid, preferably 2-ethylhexyl salicylate, 4-isopropylbenzyl salicylate, homomethyl salicylate, derivatives of benzophenone, preferably 2-hydroxy-4-methoxybenzophenone, 2-hydroxy-4-methoxy-4'-methylbenzophenone, 2,2'-dihydroxy-4-methoxybenzophenone, esters of benzalmalonic acid, preferably di(2-ethylhexyl) 4-methoxybenzalmalonate, 2,4,6-trianilino-(p-carbo-2'-ethyl-1'-hexyloxy)-1,3,5-triazine. Advantageous water-soluble UVB filters are, for example, salts of 2-phenylbenzimidazole-5-sulphonic acid, such as the sodium, potassium or triethanolammonium salt thereof, and also the sulphonic acid itself; sulphonic acid derivatives of benzophenones, preferably 2-hydroxy-4-methoxybenzophenone-5-sulphonic acid and salts thereof; sulphonic acid derivatives of 3-benzylidenecamphor, such as, for example, 4-(2-oxo-3-bornylidenemethyl)benzenesulphonic acid, 2-methyl-5-(2-oxo-3-bornylidene-methyl)sulphonic acid and salts thereof and also 1,4-di(2-oxo-10-sulpho-3-bornylidenemethyl)-benzene and salts thereof (the corresponding 10-sulphato compounds, for example the corresponding sodium, potassium or triethanolammonium salt) and also benzene-1,4-di(2-oxo-3-bornylidene)methyl-10-sulphonic acid.

The above list of the said UVB filters that can be used in combination with the synergistic mixtures of 1,2-alkanediols according to the invention should, of course, not be understood as definitive. It can also be advantageous to employ UVA filters, such as are customarily contained in cosmetic formulations. These substances are preferably derivatives of dibenzoylmethane, in particular 1-(4'-tert.-butylphenyl)-3-(4'-methoxyphenyl)-propane-1,3-dione and 1-phenyl-3-(4'-isopropylphenyl)propane-1,3-dione.

In cosmetic formulations, the synergistic mixtures of 1,2-alkanediols according to the invention can advantageously be combined with cosmetic auxiliaries, such as are customarily used in such formulations, thus, for example, with: antioxidants; perfume oils; agents to prevent foaming; colourants; pigments that have a colouring action; thickeners; surface-active substances; emulsifiers; plasticizing substances; moistening and/or moisture-retaining substances; fats, oils, waxes; other conventional constituents of a cosmetic formulation, such as alcohols, polyols, polymers, foam stabilisers; electrolytes, organic solvents or silicone derivatives.

A high content of treatment substances is usually advantageous in formulations containing synergistically active mixtures of 1,2-alkanediols for the topical prophylactic or cosmetic treatment of the skin. According to a preferred embodiment, the compositions contain one or more animal and/or vegetable treatment fats and oils, such as olive oil, sunflower oil, purified soya oil, palm oil, sesame oil, rapeseed oil, almond oil, borage oil, evening primrose oil, coconut oil, shea butter, jojoba oil, sperm oil, beef tallow, neatsfood oil and lard, and also optionally further treatment constituents, such as, for example, fatty alcohols having 8-30 C atoms. Here the fatty alcohols can be saturated or unsaturated and straight-chain or branched. For example, decanol, decenol, octanol, octenol, dodecanol, dodecenol, octadienol, decadienol, dodecadienol, oleyl alcohol, ricinol alcohol, erucic alcohol, stearyl alcohol, isostearyl alcohol, cetyl alcohol, lauryl alcohol, myristyl alcohol, arachidyl alcohol, capryl alcohol, capric alcohol, linoleyl alcohol, linolenyl alcohol and behenyl alcohol, as well the guerbet alcohols thereof can be used, in which context it would be possible to extend the list virtually arbitrarily by further structurally chemically related alcohols. The fatty alcohols preferably originate from natural fatty acids, and usually are prepared from the corresponding esters of the fatty acids by reduction. Furthermore, fatty alcohol fractions that are formed from naturally occurring fats and fat oils by reduction, such as, for example, beef tallow, peanut oil, colza oil, cottonseed oil, soya oil, sunflower oil, palm kernel oil, linseed oil, maize oil, castor oil, rapeseed oil, sesame oil, cocoa butter and cocoa fat, can be used.

In addition, the treatment substances that can preferably be combined with the synergistic mixtures of 1,2-alkanediols according to the invention also include ceramides, ceramides being understood to be N-acylsphingosines (fatty acid amides of sphingosine) or synthetic analogues of such lipids (so-called pseudo-ceramides), which clearly improve the water retention capacity of the stratum corneum.

phospholipids, for example soya lecithin, egg lecithin and cephalins vaseline, paraffin and silicone oils; the latter include, inter alia, dialkyl- and alkylaryl-siloxanes, such as dimethylpolysiloxane and methylphenylpolysiloxane, as well as the alkoxylated and quaternised derivatives thereof.

Animal and/or vegetable hydrolysed proteins can advantageously also be added to the synergistic mixtures of 1,2-alkanediols according to the invention. In this regard, in particular elastin, collagen, keratin, lactoprotein, soya protein, oat protein, pea protein, almond protein and wheat protein fractions or corresponding hydrolysed proteins, but also the condensation products thereof with fatty acids, and also quaternised hydrolysed proteins are advantageous, the use of vegetable hydrolysed proteins being preferred.

Insofar as a cosmetic or dermatological formulation containing a synergistic mixture of 1,2-alkanediols according to the invention is a solution or lotion, the solvents used can be:

water or aqueous solutions;

fatty oils, fats, waxes and other natural and synthetic fatty bodies, preferably esters of fatty acids with alcohols having a low C number, for example with isopropanol, propylene glycol or glycerol, or esters of fatty alcohols with alkanoic acids having a low C number or with fatty acids;

alcohols, diols or polyols having a low C number, as well as the ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products. In particular, mixtures of the abovementioned solvents are used. In the case of alcoholic solvents, water can be a further constituent.

Cosmetic formulations that contain synergistic mixtures of 1,2-alkanediols according to the invention can also contain antioxidants, it being possible to use all antioxidants suitable or customary for cosmetic and/or dermatological applications. Advantageously, the antioxidants are selected from the group consisting of amino acids (for example glycine, histidine, tyrosine, tryptophan) and the derivatives thereof, imidazoles (for example urocanic acid) and the derivatives thereof, peptides such as D,L-carnosine, D-carnosine, L-carnosine and the derivatives thereof (for example anserine), carotinoids, carotenes (for example α-carotene, β-carotene, lycopene) and the derivatives thereof, lipoic acid and the derivatives therefore (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl, lauryl, palmitoyl, oleyl, γ-linoleyl, cholesteryl and glyceryl esters thereof) as well as the salts thereof, dilauryl thiodipropionate, distearyl thiodipropionate, thiodipropionic acid and the derivatives thereof (esters, ethers, peptides, lipids, nucleotides, nucleosides and salts) and also sulphoximine compounds (for example buthionine sulphoximines, homocysteine sulphoximine, buthionine sulphones, penta-, hexa-, hepta-thionine sulphoximine) in very low tolerated doses, and also (metal) chelating agents, for example α-hydroxy fatty acids, palmitic acid, phytic acid, lactoferrin, α-hydroxy acids (for example citric acid, lactic acid, malic acid), humic acid, bile acid, bile extracts, bilirubin, biliverdin, EDTA, EGTA and the derivatives thereof, unsaturated fatty acids and the derivatives thereof (for example γ-linolenic acid, linoleic acid, oleic acid), folic acid and the derivatives thereof, ubiquinone and ubiquinol and the derivatives thereof, Vitamin C and derivatives (for example ascorbyl palmitate, Mg ascorbyl phosphate, ascorbyl acetate), tocopherols and the derivatives thereof (for example Vitamin E acetate, Vitamin A and the derivatives thereof (Vitamin A palmitate) and also coniferyl benzoate of benzoin resin, rutinic acid and the derivatives thereof, ferrulic acid and the derivatives thereof, butylhydroxytoluene, butylhydroxyanisole, nordihydroguaiacic acid, nordihydroguaiaretic acid, trihydroxybutyrophenone, uric acid and the derivatives thereof, mannose and the derivatives thereof, zinc and the derivatives thereof (for example ZnO, $ZnSO_4$, selenium and the derivatives thereof (for example selenium methionine), stilbenes and the derivatives thereof (for example stilbene oxide, trans-stilbene oxide) and also derivatives (salts, esters, ethers, sugars, nucleotides, nucleosides, peptides and lipids) of the said active compounds.

Cosmetic formulations that contain synergistic mixtures of 1,2-alkanediols according to the invention can also contain vitamins and vitamin precursors, it being possible to use all vitamins and vitamin precursors suitable or customary for cosmetic and/or dermatological applications. Mention may be made here in particular of vitamins and vitamin precursors such as tocopherols, Vitamin A, nicotinic acid and nicotinomide, further vitamins of the B complex, in particular biotin, and Vitamin C, pantothenyl alcohol and the derivatives thereof, in particular esters and ethers of pantothenyl alcohol, and also derivatives of pantothenyl alcohols obtained cationically, such as, for example, pantothenyl alcohol triacetate, pantothenyl alcohol, monoethyl ether and the mono acetate thereof and also cationic pantothenyl alcohol derivatives.

Cosmetic formulations that contain synergistic mixtures of 1,2-alkanediols according to the invention can also contain anti-inflammatory active compounds and/or active compounds that alleviate reddening and/or itching. In this context all anti-inflammatory active compounds and active compounds that alleviate reddening and/or itching that are suitable or customary for cosmetic and/or dermatological applications can be used. Advantageously, the anti-inflammatory active compounds and active compounds alleviating reddening and/or itching that are used are steroidal anti-inflammatory substances of the corticosteroid type, such as, for example, hydrocortisone, dexamethasone, dexamethasone phosphate, methylprednisolone or cortisone, it being possible to expand the list by adding further steroidal anti-inflammatory agents. Non-steroidal anti-inflammatory agents can also be used. Oxicams, such as piroxicam or tenoxicam; salicylates, such as aspirin, Disalcid, Solprin or fendosal; acetic acid derivatives, such as diclofenac, fenclofenac, indomethacin, sulindac, tolmetin, or clindanac; fenamates, such as mefenamic, meclofenamic, flufenamic or niflumic; propionic acid derivatives, such as ibuprofen, naproxen, benoxaprofen or pyrazoles, such as phenylbutazone, oxyphenylbutazone, febrazone or azapropazone, may be mentioned here by way of example. Alternatively, natural anti-inflammatory substances and substances that alleviate reddening and/or itching can be used. Plant extracts, special highly active plant extract fractions and also highly pure active substances isolated from plant extracts can be used. Extracts, fractions and active substances from camomile, aloe vera, *Commiphora* species, *Rubia* species, willows, willow-herb, oats and pure substances such as, inter alia, bisabolol, apigenin-7-glucoside, boswellic acid, phytosterols, glycyrrhizine, glabridin or licochalkon A are particularly preferred. The formulations containing synergistic mixtures of 1,2-alkanediols can also contain mixtures of two or more anti-inflammatory active compounds.

Cosmetic formulations that contain synergistic mixtures of 1,2-alkanediols according to the invention can also contain further active compounds having a skin lightening action. In this context all skin lightening active compounds that are suitable or customary for cosmetic and/or dermatological applications can be used according to the invention. Advantageous skin lightening active compounds are, to this extent, kojic acid, hydroquinone, arbutin, ascorbic acid, magnesium ascorbylphosphate, liquorice root extracts and the constituents thereof glabridin or licochalkon A, extracts from *Rumex* and *Ramulus* species, extracts from pine species (*Pinus*) and extracts from *Vitis* species, which, inter alia, contain skin-lightening stilbene derivatives.

Cosmetic formulations that contain synergistic mixtures of 1,2-alkanediols according to the invention can also contain active compounds having a skin-tanning action. To this extent all skin-tanning active compounds that are suitable or customary for cosmetic and/or dermatological applications can be used. Dihydroxyacetone (DHA; 1,3-dihydroxy-2-propanone) may be mentioned here by way of example. DHA can be either in monomer or in dimer form, the proportion of dimers predominating in crystalline form.

Cosmetic formulations that contain synergistic mixtures of 1,2-alkanediols according to the invention can also contain mono- di- and oligo-saccharides, such as, for example, glucose, galactose, fructose, mannose, and lactose.

Cosmetic formulations that contain synergistic mixtures of 1,2-alkanediols according to the invention can also contain plant extracts, which are usually prepared by extraction of the complete plant, but in individual cases are also prepared exclusively from blossom and/or leaves, wood, bark or roots of the plant. With regard to the plant extracts that can be used, reference is made in particular to the extracts that are listed in the table starting on page 44 of the third edition of the Leitfaden zur Inhaltsstoffdeklaration kosmetischer Mittel, (Guide to the Declaration of Constituents of Cosmetic Agents), published by the Industrieverband Körperpflegemittel und Waschmittel e.V. (IKW), Frankfurt. The extracts from aloe, Hamamelis, algae, oak bark, willow-herb, stinging nettles, dead nettles, hops, camomile, milfoil, arnica, calendula, burdock root, horse-tail, hawthorn, linden blossom, almonds, pine needles, horsechestnut, sandalwood, juniper, coconut, mango, apricot, orange, lemon, lime, grapefruit, apple, green tea, grapefruit seed, wheat, oats, barley, sage, thyme, basil, rosemary, birch, mallow, bitter-crass, willow bark, restharrow, coltsfoot, althaea, ginseng and ginger root are particularly advantageous. Amongst these, the extracts from aloe vera, camomile, algae, rosemary. calendula, ginseng, cucumber, sage, stinging nettles, linden blossom, arnica and Hamamelis are particularly preferred. Mixtures of two or more plant extracts can also be employed. Extraction agents that can be used for the preparation of the said plant extracts can be, inter alia, water, alcohols and mixtures thereof. Amongst the alcohols, lower alcohols, such as ethanol and isopropanol, but also polyhydric alcohols, such as ethylene glycol, propylene glycol and butylene glycol are preferred in this context, and specifically both as sole extracting agent and also in mixtures with water. The plant extracts can be used in the pure form or also in dilute form.

Cosmetic formulations that contain synergistic mixtures of 1,2-alkanediols according to the invention can also contain anionic, cationic, non-ionic and/or amphoteric surfactants, especially if crystalline or microcrystalline solids, for example inorganic micropigments, are to be incorporated into the formulations. Surfactants are amphiphilic substances that are able to dissolve organic, non-polar substances in water. In this context the hydrophilic parts of a surfactant molecule are usually polar functional groups, for example, —$COO^-$, —$OSO_3^{2-}$, —$SO_3^-$, whilst the hydrophobic parts are as a rule non-polar hydrocarbon radicals. Surfactants are generally classified according to the nature and charge of the hydrophilic part of the molecule. Four groups can be differentiated here:

anionic surfactants, cationic surfactants, amphoteric surfactants and non-ionic surfactants.

Anionic surfactants usually contain carboxylate, sulphate or sulphonate groups as functional groups. In aqueous solution they form negatively charged organic ions in the acid or neutral medium. Cationic surfactants are characterised virtually exclusively by the presence of a quaternary ammonium group. In aqueous solution they form positively charged organic ions in the acid or neutral medium. Amphoteric surfactants contain both anionic and cationic groups and accordingly behave like anionic or cationic surfactants in aqueous solutions, depending on the pH value. They have a positive charge in a strongly acid medium and a negative charge in an alkaline medium. In the neutral pH range, on the other hand, they are zwitter ionic. Polyether chains are typical of non-ionic surfactants. Non-ionic surfactants do not form ions in an aqueous medium.

A. Anionic Surfactants

Anionic surfactants that can advantageously be used are acylamino acids (and the salts thereof), such as acylglutamates, for example, sodium acylgultamate, di-TEA-palmitoyl aspartate and sodium capryl/caprin glutamate, acylpeptides, for example, palmitoyl-hydrolysed lactoprotein, sodium cocoyl-hydrolysed soya protein and sodium/potassium cocoyl-hydrolysed collagen, sarcosinates, for example, myristoyl sarcosine, TEA lauroyl sarcosinate, sodium lauroyl sarcosinate and sodium cocoyl sarcosinate, taurates, for example, sodium lauroyl taurate and sodium methylcocoyl taurate, acyl lactylates, lauroyl lactylate, caproyl lactylate alaninates carboxylic acids and derivatives, such as, for example, lauric acid, aluminium stearate, magnesium alkanolate and zinc undecylenate, ester-carboxylic acids, for example calcium stearoyl lactylate, laureth-6 citrate and sodium PEG-4 lauramidocarboxylate, ether-carboxylic acids, for example sodium laureth-13 carboxylate and sodium PEG-6 cocamide carboxylate, phosphoric acid esters and salts, such as, for example, DEA-oleth-10 phosphate and dilaureth-4 phosphate, sulphonic acids and salts, such as acyl isothionates, for example sodium/ammonium cocoyl-isethionate, alkylarylsulphonates, alkylsulphonates, for example sodium coconut monoglyceride sulphate, sodium $C_{12-14}$ olefin-sulphonate sodium lauryl sulphoacetate and magnesium PEG-3 cocamidosulphate, sulphosuccinates, for example, dioctylsodium sulphosuccinate, disodium laureth-sulphosuccinate, disodium laurylsulphosuccinate and disodium undecylenamido MEA-sulphosuccinate and sulphuric acid esters, such as alkyl ether sulphate, for example, sodium, ammonium, magnesium, MIPA, TIPA laureth sulphate, sodium myreth sulphate and sodium C12-13 pareth sulphate, alkyl sulphates, for example, sodium, ammonium and TEA lauryl sulphate.

B. Cationic Surfactants

Cationic surfactants that can advantageously be used are alkylamines, alkylimidazoles, ethoxylated amines and quaternary surfactants $RNH_2CH_2CH_2COO^-$ (at pH=7)

$RNHCH_2CH_2COO$—$B^+$ (at pH=12) $B^+$=arbitrary cation, for example $Na^+$ esterquats Quaternary surfactants contain at least one N atom that is covalently bonded to 4 alkyl or aryl groups. This leads to a positive charge, irrespective of the pH value. Alkylbetaine, alkylamidopropylbetaine and alkylamidopropyl-hydroxysulfaine are advantageous. The cationic surfactants used can furthermore preferably be chosen from the group comprising the quaternary ammonium compounds, in particular benzyltrialkyl-ammonium chloride or bromide, such as, for example, benzyldimethylstearyl-ammonium chloride, and also alkyltrialkylammonium salts, for example cetyltrimethylammonium chloride or bromide, alkyldimethylhydroxyethylammonium chlorides or bromides, dialkyldimethylammonium chlorides or bromides, alkylamidoethyltrimethylammonium ether sulphates, alkylpyridinium salts, for example lauryl- or cetyl-pyrimidinium chloride, imidazoline derivatives and compounds of a cationic nature, such as amine oxides, for example alkyldimethylamine oxides or alkylaminoethyldimethylamine oxides. Cetyltrimethyl-ammonium salts can be used particularly advantageously.

C. Amphoteric Surfactants

Amphoteric surfactants that can advantageously be used are
acyl-/dialkylethylenediamine, for example sodium acylamphoacetate, disodium acylamphodipropionate, disodium alkylamphodiacetate, sodium acylamphohydroxypropylsulphonate, disodium acylampho-diacetate and sodium acylamphopropionate,
N-alkylamino acids, for example aminopropylalkylglutamide, alkylaminopropionic acid, sodium alkylimidodipropionate and lauroamphocarboxyglycinate.

D. Non-Ionic Surfactants

Non-ionic surfactants that can advantageously be used are
alcohols,
alkanolamides, such as cocamides MEA/DEA/MIPA,
amine oxides, such as cocoamidopropylamine oxide,
esters, that are formed by esterification of carboxylic acids with ethylene oxide, glycerol, sorbitan or other alcohols,
ethers, for example ethoxylated/propoxylated alcohols, ethoxylated/propoxylated esters, ethoxylated/propoxylated glycerol esters, ethoxylated/propoxylated cholesterols, ethoxylated/propoxylated triglyceride esters, ethoxylated [lacuna] propoxylated lanolin, ethoxylated/propoxylated polysiloxanes, propoxylated POE ethers and alkylpolyglycosides, such as lauryl glucoside, decyl glycoside and coco glycoside.
sucrose esters and ethers
polyglycerol esters, diglycerol esters, monoglycerol esters
methylglucose esters, esters of hydroxy acids The use of a combination of anionic and/or amphoteric surfactants with one or more non-ionic surfactants is also advantageous. The surface-active substance can be present in a concentration of between 1 and 98% (m/m) in the formulations according to the invention containing synergistic mixtures of 1,2-alkanediols, based on the total weight of the formulations.

Cosmetic or dermatological formulations that contain synergistic mixtures of 1,2-alkanediols according to the invention according to the invention can also be in the form of emulsions.

The oil phase can advantageously be chosen from the following group of substances:
mineral oils, mineral waxes
fatty oils, fats, waxes and other natural and synthetic fatty bodies, preferably esters of fatty acids with alcohols having a low C number, for example with isopropanol, propylene glycol or glycerol, or esters of fatty alcohols with alkanoic acids having a low C number or with fatty acids;
alkyl benzoates;
silicone oils, such as dimethylpolysiloxanes, diethylpolysiloxanes, diphenylpolysiloxanes and mixed forms therefrom.

Advantageously, (a) esters of saturated and/or unsaturated, branched and/or straight-chain alkanecarboxylic acids having a chain length of 3 to 30 C atoms and saturated and/or unsaturated, branched and/or straight-chain alcohols having a chain length of 3 to 30 C atoms, (b) esters of aromatic carboxylic acids and saturated and/or unsaturated, branched and/or straight-chain alcohols having a chain length of 3 to 30 C atoms can be used. Preferred ester oils are isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of such esters, for example, jojoba oil.

Furthermore, the oil phase can advantageously be chosen from the group comprising the branched and straight-chain hydrocarbons and waxes, the silicone oils, the dialkyl ethers, the group comprising the saturated or unsaturated, branched or straight-chain alcohols, and also the fatty acid triglycerides, specifically, the triglycerol esters of saturated and/or unsaturated, branched and/or straight-chain alkanecarboxylic acids having a chain length of 8 to 24, in particular 12 to 18 C atoms. The fatty acid triglycerides can advantageously be chosen from the group comprising the synthetic, semi-synthetic and natural oils, for example, olive oil, sunflower oil, soya oil, peanut oil, rapeseed oil, almond oil, palm oil, coconut oil, palm kernel oil and more of the like. Arbitrary admixtures of such oil and wax components can also advantageously be used. In some cases it is also advantageous to use waxes, for example cetyl palmitate, as the sole lipid component of the oil phase; advantageously, the oil phase is chosen from the group that consists of 2-ethylhexyl isostearate, octyldodecanol, isotridecyl isononanoate, isoeicosane, 2-ethylhexyl cocoate, $C_{12\text{-}15}$-alkyl benzoate, capryl-capric acid triglyceride and dicaprylyl ether. Mixtures of $C_{12\text{-}15}$-alkyl benzoate and 2-ethylhexyl isostearate, mixtures of $C_{12\text{-}15}$-alkyl benzoate and isotridecyl isononanoate and mixtures of $C_{12\text{-}15}$-alkyl benzoate, 2-ethylhexyl isostearate and isotridecyl isononanoate are particularly advantageous. The hydrocarbons paraffin oil, squalane and squalene can also advantageously be used. Advantageously, the oil phase can furthermore contain cyclic or linear silicone oils or consist entirely of such oils, it being, however, preferred to use an additional content of other oil phase components in addition to the silicone oil or the silicone oils. Cyclomethicone (for example, decamethylcyclopentasiloxane) can advantageously be used as silicone oil. However, other silicone oils can also advantageously be used, for example undecamethylcyclotrisiloxane, polydimethylsiloxane and poly(methylphenylsiloxane). Furthermore, mixtures of cyclomethicone and isotridecyl isononanoate and of cyclomethicone and 2-ethylhexyl isostearate are particularly advantageous.

The aqueous phase of formulations that according to the invention contain synergistic mixtures of 1,2-alkanediols and are in the form of an emulsion can comprise: alcohols, diols or polyols having a low C number and also the ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and also alcohols having a low C number, for example, ethanol, isopropanol, 1,2-propanediol, glycerol and also, in particular, one or more thickeners, which thickener or thickeners can advantageously be chosen from the group comprising silicon dioxide, aluminium silicates, polysaccharides and the derivatives thereof, for example hyaluronic acid, xanthan gum, hydroxypropyl-methylcellulose, and particularly advantageously from the group comprising the polyacrylates, preferably a polyacrylate from the group comprising the so-called carbopols, for example carbopols of types 980, 981, 1382, 2984, 5984, in each case on their own or in combination.

Formulations that contain synergistic mixtures of 1,2-alkanediols according to the invention and are in the form of an emulsion advantageously contain one or more emulsifiers. O/W emulsifiers can, for example, advantageously be chosen from the group comprising the polyethoxylated or polypropoxylated or polyethoxylated and polypropoxylated products, for example:

the fatty alcohol ethoxylates
the ethoxylated wool wax alcohols,
the polyethylene glycol ethers of the general formula $$R-O-(-CH_2-CH_2-O-)_n-R',$$

the fatty acid ethoxylates of the general formula $$R-COO-(-CH_2-CH_2-O-)_n-H,$$

the etherified fatty acid ethoxylates of the general formula $$R-COO-(-CH_2-CH_2-O-)_n-R',$$

the esterified fatty acid ethoxylates of the general formula $$R-COO-(-CH_2-CH_2-O-)_n-C(O)-R',$$

the polyethylene glycol glycerol fatty acid esters
the ethoxylated sorbitan esters
the cholesterol ethoxylates
the ethoxylated triglycerides
the alkyl ether carboxylic acids of the general formula $$R-COO-(-CH_2-CH_2-O-)_n-OOH,$$

and n represents a number from 5 to 30,
the polyoxyethylene sorbitol fatty acid esters,
the alkyl ether sulphates of the general formula $$R-O-(-CH_2-CH_2-O-)_n-SO_3-H$$

the fatty alcohol propoxylates of the general formula $$R-O-(-CH_2-CH(CH_3)-O-)_n-H$$

the polypropylene glycol ethers of the general formula $$R-O-(-CH_2-CH(CH_3)-O-)_n-R'$$

the propoxylated wool wax alcohols,
the esterified fatty acid propoxylates $$R-COO-(-CH_2-CH(CH_3)-O-)_n-R'$$

the esterified fatty acid propoxylates of the general formula $$R-COO-(-CH_2-CH(CH_3)-O-)_n-C(O)-R'$$

the fatty acid propoxylates of the general formula $$R-COO-(-CH_2-CH(CH_3)-O-)_n-H,$$

the polypropylene glycol glycerol fatty acid esters
the propoxylated sorbitan esters
the cholesterol propoxylates
the propoxylated triglycerides
the alkyl ether carboxylic acids of the general formula $$R-O-(-CH_2-CH(CH_3)-O-)_n-CH_2-COOH,$$

the alkyl ether sulphates and the acids on which these sulphates are based of the general formula $$R-O-(-CH_2-CH(CH_3)-O-)_n-SO_3-H,$$

the fatty alcohol ethoxylates/propoxylates of the general formula $$R-O-X_n-Y_m-H$$

the polypropylene glycol ethers of the general formula $$R-O-X_n-Y_m-R'$$

the esterified fatty acid propoxylates of the general formula $$R-COO-X_n-Y_m-R'$$

the fatty acid ethoxylates/propoxylates of the general formula $$R-COO-X_n-Y_m-H.$$

According to the invention, the polyethoxylated or polypropoxylated or polyethoxylated and polypropoxylated O/W emulsifiers used are particularly advantageously chosen from the group comprising substances having HLB values of 11-18, very particularly advantageously having HLB values of 14.5-15.5, insofar as the O/W emulsifiers contain saturated radicals R and R'. If the O/W emulsifiers contain unsaturated radicals R and/or R', or if there are isoalkyl derivatives, the preferred HLB value of such emulsifiers can also be lower or higher.

It is advantageous to choose the fatty alcohol ethoxylates from the group comprising the ethoxylated stearyl alcohols, cetyl alcohols, cetylstearyl alcohols (cetearyl alcohols). The following are particularly preferred:

polyethylene glycol(13) stearyl ether (Steareth-13),
polyethylene glycol(14) stearyl ether (Steareth-14),
polyethylene glycol(15) stearyl ether (Steareth-15),
polyethylene glycol(16) stearyl ether (Steareth-16),
polyethylene glycol(17) stearyl ether (Steareth-17),
polyethylene glycol(18) stearyl ether (Steareth-18),
polyethylene glycol(19) stearyl ether (Steareth-19),
polyethylene glycol(20) stearyl ether (Steareth-20),
polyethylene glycol(12) isostearyl ether (Isosteareth-12),
polyethylene glycol(13) isostearyl ether (Isosteareth-13),
polyethylene glycol(14) isostearyl ether (Isosteareth-14),
polyethylene glycol(15) isostearyl ether (Isosteareth-15),
polyethylene glycol(16) isostearyl ether (Isosteareth-16),
polyethylene glycol(17) isostearyl ether (Isosteareth-17),
polyethylene glycol(18) isostearyl ether (Isosteareth-18),
polyethylene glycol(19) isostearyl ether (Isosteareth-19),
polyethylene glycol(20) isostearyl ether (Isosteareth-20),
polyethylene glycol(13) cetyl ether (Ceteth-13),
polyethylene glycol(14) cetyl ether (Ceteth-14),
polyethylene glycol(15) cetyl ether (Ceteth-15),
polyethylene glycol(16) cetyl ether (Ceteth-16),
polyethylene glycol(17) cetyl ether (Ceteth-17),
polyethylene glycol(18) cetyl ether (Ceteth-18),
polyethylene glycol(19) cetyl ether (Ceteth-19),
polyethylene glycol(20) cetyl ether (Ceteth-20),
polyethylene glycol(13) isocetyl ether (Isoceteth-13), polyethylene glycol(14) isocetyl ether (Isoceteth-14), polyethylene glycol(15) isocetyl ether (Isoceteth-15), polyethylene glycol(16) isocetyl ether (Isoceteth-16), polyethylene glycol(17) isocetyl ether (Isoceteth-17), polyethylene glycol(18) isocetyl ether (Isoceteth-18), polyethylene glycol(19) isocetyl ether (Isoceteth-19), polyethylene glycol(20) isocetyl ether (Isoceteth-20), polyethylene glycol(12) oleyl ether (Oleth-12), polyethylene glycol(13) oleyl ether (Oleth-13), polyethylene glycol(14) oleyl ether (Oleth-14), polyethylene glycol(15) oleyl ether (Oleth-15), polyethylene glycol(12) lauryl ether (Laureth-12), polyethylene glycol(12) isolauryl ether (Isolaureth12), polyethylene glycol(13) cetyl stearyl ether (Ceteareth-13), polyethylene glycol(14) cetyl stearyl ether (Ceteareth-14), polyethylene glycol(15) cetyl stearyl ether (Ceteareth-15), polyethylene glycol(16) cetyl stearyl ether (Ceteareth-16), polyethylene glycol(17) cetyl stearyl ether (Ceteareth-17), polyethylene glycol(18) cetyl stearyl ether (Ceteareth-18), polyethylene glycol(19) cetyl stearyl ether (Ceteareth-19), polyethylene glycol(20) cetyl stearyl ether (Ceteareth-20).

It is furthermore advantageous to choose the fatty acid ethoxylates from the following group:

polyethylene glycol(20) stearate, polyethylene glycol(21) stearate, polyethylene glycol(22) stearate, polyethylene glycol(23) stearate, polyethylene glycol(24) stearate, polyethylene glycol(25) stearate, polyethylene glycol(12) isostearate, polyethylene glycol(13) isostearate, polyethylene glycol(14) isostearate, polyethylene glycol(15) isostearate, polyethylene glycol(16) isostearate, polyethylene glycol(17) isostearate, polyethylene glycol(18) isostearate, polyethylene glycol(19) isostearate, polyethylene glycol(20) isostearate, polyethylene glycol(21) isostearate, polyethylene glycol(22) isostearate, polyethylene glycol(23) isostearate, polyethylene glycol(24) isostearate, polyethylene glycol(25) isostearate, polyethylene glycol(12) oleate, polyethylene glycol(13) oleate, polyethylene glycol(14) oleate, polyethylene glycol(15) oleate, polyethylene glycol(16) oleate, polyethylene glycol(17) oleate, polyethylene glycol(18) oleate, polyethylene glycol(19) oleate, polyethylene glycol(20) oleate.

Advantageously, sodium laureth-11-carboxylate can be used as ethoxylated alkyl ether carboxylic acid or the salt thereof. Sodium laureth 1-4 sulphate can advantageously be used as alkyl ether sulphate. Polyethylene glycol(30) cholesteryl ether can advantageously be used as ethoxylated cholesterol derivative. Polyethylene glycol(25) soyasterol has also proved useful. The polyethylene glycol(60) evening primrose glycerides can advantageously be used as ethoxylated triglycerides.

It is furthermore advantageous to choose the polyethylene glycol glycerol fatty acid esters from the group comprising polyethylene glycol(20) glyceryl laurate, polyethylene glycol(21) glyceryl laurate, polyethylene glycol(22) glyceryl laurate, polyethylene glycol(23) glyceryl laurate, polyethylene glycol(6) glyceryl caprate/caprinate, polyethylene glycol(20) glyceryl oleate, polyethylene glycol(20) glyceryl isostearate, polyethylene glycol(18) glyceryl oleate/cocoate.

It is also advantageous to choose the sorbitan esters from the group comprising polyethylene glycol(20) sorbitan monolaurate, polyethylene glycol(20) sorbitan monostearate, polyethylene glycol(20) sorbitan monoisostearate, polyethylene glycol(20) sorbitan monopalmitate, polyethylene glycol(20) sorbitan monooleate.

The following can be used as advantageous W/O emulsifiers: fatty alcohols having 8 to 30 carbon atoms, monoglycerol esters of saturated and/or unsaturated, branched and/or straight-chain alkanecarboxylic acids having a chain length of 8 to 24, in particular 12 to 18 C atoms, diglycerol esters of saturated and/or unsaturated, branched and/or straight-chain alkanecarboxylic acids having a chain length of 8 to 24, in particular 12 to 18 C atoms, monoglycerol ethers of saturated and/or unsaturated, branched and/or straight-chain alcohols having a chain length of 8 to 24, in particular 12 to 18 C atoms, diglycerol ethers of saturated and/or unsaturated, branched and/or straight-chain alcohols having a chain length of 8 to 24, in particular 12 to 18 C atoms, propylene glycol esters of saturated and/or unsaturated, branched and/or straight-chain alkanecarboxylic acids having a chain length of 8 to 24, in particular 12 to 18 C atoms and sorbitan esters of saturated and/or unsaturated, branched and/or straight-chain alkanecarboxylic acids having a chain length of 8 to 24, in particular 12 to 18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol(2) stearyl ether (Steareth-2), glyceryl monolaurate, glyceryl monocaprinate, glyceryl monocaprylate.

The invention will be explained in more detail below on the basis of examples, with reference to the appended figure:

EXAMPLE 1

Testing of Adequate Preservation by Synergistically Active 1,2-diol-mixtures A test for adequate preservation was carried out in accordance with the European Pharmacopea.

The test thus consists of the contamination of the formulation, if possible in its final ratio, with a prescribed inoculum of suitable microorganisms, storage of the inoculated formulation at a specific temperature, taking of samples from the vessel at specific intervals and determination of the number of microorganisms in the samples taken in this way. The preserving properties are adequate if, under the conditions of the test, there is a distinct reduction or optionally no increase in the germ count in the inoculated formulations after the prescribed times at the prescribed temperatures. Experimental details of the test procedure are described in the European Pharmacopea (ISBN 3-7692-2768-9; 2001 supplement to the 3rd Edition, page 421-422, chapter 5.1.3).

Test Germs:

The following microorganism strains were used for the tests for adequate preservation:

A: *Escherichia coli* ATCC 8739

B: *Pseudomonas aeruginosa* ATCC 9027

C: *Staphylococcus aureus* ATCC 6538

D: *Candida albicans* ATCC 10231

E: *Aspergillus niger* ATCC 16404

The initial germ count (CFU/g; "0" value) was in the range of 240,000 to 300,000 in the various test series.

Formulation:

For the tests for adequate preservation, (a) potentially synergistically active mixtures taken into account and (b), for comparison purposes, the corresponding unmixed 1,2-diols were incorporated in O/W emulsions.

Table 2 shows, by way of example, the formulation for a mixture according to the invention consisting of 1,2-hexanediol (2%) and 1,2-octanediol (1%). The variation in the total concentration of 1,2-diols or 1,2-diol mixtures in the O/W emulsions was compensated for by increasing or reducing the water content, so that otherwise identical formulations always comprised 100 parts by weight in total.

TABLE 2

Example of a formulation for a O/W emulsion containing a 1,2-hexanediol (2%)/1,2-octanediol (1%) mixture

| Raw material (Tradename indicated in some cases) | Manufacturer | % (m/m) |
|---|---|---|
| Water, low-germ | | 76.1 |
| Citric acid, 10% | | 0.4 |
| Dragophos S | DRAGOCO | 2 |
| PCL Liquid | DRAGOCO | 3 |
| Isodragol | DRAGOCO | 7 |
| Lanette 18 | COGNIS | 4.5 |
| Dracorin GMS | DRAGOCO | 2 |
| Dow Corning 200 fluid | Dow Corning | 2 |
| 1,2-hexanediol | | 2 |
| 1,2-octanediol | | 1 |
| Total | | 100 |

Result:

The results of the preservative loading tests for the 1,2-diols and 1,2-diol mixtures tested are given in Table 3. Surprisingly, it was found that 1,2-diol mixtures consisting of defined mass ratios of 1,2-pentanediol, 1,2-hexanediol, 1,2-octanediol and/or 1,2-decanediol have a far greater activity than the individual substances metered in the same concentration. This is shown, in particular, in the residual germ counts remaining after 28 days. Binary and ternary mixtures of 1,2-hexanediol with 1,2-pentanediol and/or 1,2-octanediol proved to be particularly effective here. In the case of all 5 test germs (*Escherichia coli, Pseudomonas aeruginosa, Staphylococcus aureus, Candida albicans* and *Aspergillus niger*) it was possible to reduce the concentration of colony forming units (CFU) to the preferred target 0 value within the chosen time period.

As can be seen from Table 3 and FIG. 1 (test for adequate preservation for *Aspergillus niger* over a period of 28 days; logarithmic plot of the reduction in the germ count for 1,2-hexanediol (3% in O/W emulsion), for 1,2-octanediol (3%) and for a 1,2-hexanediol/1,2-octanediol mixture (mass ratio 2:1; dosage likewise 3%), it was possible in the case of *Aspergillus niger*, a germ that is particularly problematical with regard to the preservation of industrial products, to reduce the germ count to 0 within 28 days by using the mixtures according to the invention. On the other hand, the individual substances (1,2-pentanediol, 1,2-hexanediol, 1,2-octanediol and 1,2-decanediol; Table 3) tested for comparison purposes, likewise in a dosage of 3%, did not enable a reduction in the number of colony forming units (CFU) to the desired 0 value in the case of *Aspergillus niger*. The test series (FIG. 1 and Tab. 3) thus show, by way of example, that 1,2-diol mixtures consisting of at least two different members of the group that consists of 1,2-pentanediol, 1,2-hexanediol, 1,2-octanediol and 1,2-decanediol have a synergistically intensified activity.

Based on the available data, the synergistic intensification of the activity of the diol mixtures according to the invention can also be demonstrated on the basis of the Kull equation (F. C. Kull et al.; Applied Microbiology Vol. 9, p. 538-541 (1961); David C. Steinberg; Cosmetics & Toiletries Vol. 115 (No. 11), p. 59-62; November 2000; see also Table 4 for the method of calculation). The Kull equation enables the pure substances and the active compound mixtures prepared therefrom to be compared in respect of their antimicrobial activity. With this equation the so-called synergy index (SI), which is a measure for a synergistic activity, but also for a possible antagonistic activity, of a mixture having an antimicrobial action, is determined. A synergistic effect is evident if the SI value determined is less than 1. On the other hand, if an SI of precisely 1 is calculated, there is a pure additive effect of two substances having an antimicrobial action. In the case of an SI value greater than 1, on the other hand, there is a (frequently undesired) antagonistic effect.

By way of example the calculation of the SI value for the treatment of *Aspergillus niger* with a mixture of 1,2-hexanediol and 1,2-octanediol (ratio 2:1) after an incubation phase of 14 days is shown below (Table 4). The calculated SI of 0.106 clearly shows that a 2:1 mixture of 1,2-hexanediol and 1,2-octanediol is a highly synergistic combination of active compounds. It was not possible to determine the 28-day SI value since after this incubation phase the germ counts were 0 when the diol mixture was used (cf. Table 3). The Kull equation cannot be used in this particular case; however, the synergy is, of course, in any event evident on the basis of the germ count of 0.

TABLE 4

Calculation of the synergy index (SI) for 1,2-hexanediol/1,2-octanediol (Mass ratio: 2:1; dosage in O/W emulsion: 3%; test germ: *Aspergillus niger*)

|  | A<br>1,2-hexanediol | B<br>1,2-octanediol | C<br>1,2-hexanediol + 1,2-octanediol;<br>Mass ratio: 2:1 |
|---|---|---|---|
| *Aspergillus niger*:<br>14 days [CFU/ml] | 28000 | 1000 | 300 |
| Kull Equation: SI = C × D/A + C × E/B | | | |
| A: Germ count for substance A | 28000 | | |
| B: Germ count for substance B | | 1000 | |
| C: Germ count for mixture of A + B | | | 300 |
| D: Amount of A in C | | | 0.66 |
| E: Amount of B in C | | | 0.33 |
| SI: Synergy Index | | | 0.106 |

Literature: Synergy Index:
D. C. Steinberg; Cosmetics & Toiletries 115 (11); p. 59-62 (2000)
F. C. Kull et al.; Applied Microbiology 9; p. 538-541 (1961)

EXAMPLE 2

Determination of the Minimum Inhibitory Concentrations for Various Germs and Calculation of Synergy Indices on the Basis of MIC Values Preliminary Remarks:

The finding that, in addition to their use as preservatives, the 1,2-diol mixtures according to the invention are also suitable for controlling germs which, for example, are responsible for body odour goes back to test series in which the particularly relevant germs *Staphylococcus epidermidis*, *Corynebacterium xerosis* and *Brevibacterium epidermidis* were tested. In addition to the MIC values for *Staphylococcus epidermidis*, *Corynebacterium xerosis* and *Brevibacterium epidermidis*, the corresponding synergy indices of the synergistically active mixtures according to the invention were determined in these test series (cf. Table 7).

In addition, the MIC determinations showed that the 1,2-diol mixtures claimed also have a surprisingly good action against further test germs such as *Trichophyton mentagrophytes*, *Epidermophyton floccosum*, *Propionibacterium acnes*, as a result of which the diol mixtures claimed can also be used as agents against mycoses or acne.

An antagonistic effect was found only against *Malassezia furfur*.

General Test Conditions:

The antimicrobial action of 1,2-diols and of the dial mixtures according to the invention was demonstrated with the aid of the agar dilution method based on DIN 58 940/ICS and DIN 58 944/ICS. Petri dishes 9.0 cm in diameter were charged with 13.5 ml freshly prepared Mueller-Hinton agar (Merck, Ref. 1.05437 or Wilkins-Chalgren agar boullion, Oxoid, Ref. CM 643, supplemented with log agar-agar/liter) kept liquid at 50° C., to which the various concentrations of the diluted samples were added in 10% (V/V)=1.5 ml. Mueller-Hinton agar that contained 3% Tween80 (Merck, Ref. 8.22 187) was used for the test germ *Malassezia furfur*.

In each case 5 ml of the samples were diluted in distilled water and made up to 10 ml. The further test concentrations of the particular dilution series, which were prepared in the form of geometric series, were prepared by progressive 1:2 dilution of this batch with distilled water.

By means of a further dilution with the test agar (1.5 ml sample or corresponding dilutions+13.5 ml agar), 10 times lower final concentrations were achieved in each case (corresponds to an initial concentration of 50,000 ppm in each case). Two agar plates were poured per test concentration and nutrient medium.

The following controls were carried out, with two agar plates in each case:

| | |
|---|---|
| K1: 15.0 ml Mueller-Hinton agar | (not inoculated) |
| K2: 13.5 ml Mueller-Hinton agar + 1.5 ml distilled water | (inoculated) |
| K3: 13.5 ml Mueller-Hinton agar + 1.5 ml distilled water | (inoculated) |
| K4: 15.0 ml Mueller-Hinton agar | (inoculated) |
| K5: 15.0 ml Mueller-Hinton agar + 3% Tween 80 | (not inoculated) |
| K6: 13.5 ml Mueller-Hinton agar + 3% Tween 80 + 1.5 ml distilled water. | (not inoculated) |
| K7: 13.5 ml Mueller-Hinton agar + 3% Tween 80 + 1.5 ml distilled water. | (inoculated) |
| K8: 15.0 ml Mueller-Hinton agar + 3% Tween 80 | (inoculated) |
| K9: 15.0 ml Wilkins-Chalgren agar | (not inoculated) |
| K10: 13.5 ml Wilkins-Chalgren agar + 1.5 ml distilled water | (not inoculated) |
| K11: 13.5 ml Wilkins-Chalgren agar + 1.5 ml distilled water | (inoculated) |
| K12: 15.0 ml Wilkins-Chalgren agar + 1.5 ml distilled water | (inoculated) |

After solidification and drying (approx. 1 h at 37° C.), the test plates were inoculated in point form with, in each case, 1 µl of the test germ suspensions listed below. To check purity and identity the bacteria that grow aerobically (*Brevibacterium epidermidis*, *Corynebacterium xerosis*, *Staphylococcus epidermidis*) were [lacuna] on Columbia blood agar (BioMérieux, Ref. 43049). The mould *Aspergillus niger*, the yeast *Candida albicans* and the two skin fungi *Trichophyton mentagrophytes* and *Epidermophyton floccosum* were cultured on Sabouraud agar (BioMérieux, Ref. 43555). *Malassezia furfur* was cultured on Sabourad HLT agar with disinhibitors (addition of 3% Tween80: 1%; lecithin: 0.3%; histidine: 0.1%; Merck, Ref. 1.18368). *Propionibacterium acnes* was cultured on Schaedler agar (BioMérieux, Ref. 43273). Further details on the test germs can be taken from Table 5.

TABLE 5

Test germs (strain names) and germ counts

| Test germ | Strain name | CFU*/ml |
|---|---|---|
| *Brevibacterium epidermidis* | ATCC 35514 | $2.8 \times 10^7$ |
| *Corynebacterium xerosis* | ATCC 7711 | $2.1 \times 10^7$ |
| *Propionibacterium acnes* | ATCC 11829 | $2.0 \times 10^8$ |
| *Staphylococcus epidermidis* | ATCC 12228 | $2.2 \times 10^7$ |
| *Malassezia furfur* | DSM 6171 | $3.0 \times 10^7$ |
| *Epidermophyton floccosum* | CBS 55384 | $2.1 \times 10^7$ |
| *Trichophyton mentagrophtes* | CBS 26379 | $3.3 \times 10^7$ |

CFU* = colony-forming units

The preparation of the test germ suspensions of the bacterial germs that grow aerobically was carried out by incubation of Mueller-Hinton broth (Merck, Ref. 1.10293) which had been inoculated with a few individual colonies of the relevant test germs, at 36° C. After a distinct turbidity had been obtained, sterile nutrient broth was added to the suspensions in such an amount that the turbidity thereof corresponded to McFarland standard 0.5 (approx. $1.5 \times 10^8$ CFU/ml).

For preparation of the other test germ suspensions, the test strains were cultured on the abovementioned solid nutrient medium, harvested using sterile swabs and taken up or diluted in such an amount of Mueller-Hinton broth that the turbidity of the suspensions corresponded to McFarland standard 0.5.

All test germ suspensions with the exception of *Propionibacterium acnes* were diluted again 1:10 with sterile broth and the germ count thereof was determined by the surface method using a Spiralometer (results: see Table 5).

The inoculated plates were incubated under the conditions indicated in Table 6 and then evaluated. The MIC (minimum inhibitory concentration) was regarded as the lowest concentration of active compound at which macroscopically there is no growth. Minimal, barely visible growth or few small individual colonies were evaluated as inhibition.

The results shown in Table 7 show, for 1,2-hexanediol and 1,2-octanediol by way of example, the synergistic intensification of the activity of the 2:1 mixture of the two diols. Accordingly, microorganisms such as *Staphylococcus epidermidis, Brevibacterium epidermidis, Corynebacterium xerosis, Propionibacterium acnes, Trichophyton mentagrophytes* and *Epidermophyton floccosum* are also clearly more strongly inhibited by the 1,2-diol mixture in direct comparison with the corresponding individual substances. The synergy indices determined on the basis of the MIC values with the aid of the Kull equation are also shown in Table 7. The SI values clearly show that the 1,2-hexanediol/1,2-octanediol diol mixture has a synergistically intensified activity and, in

TABLE 6

Inoculation and Incubation

| Test germ | Strain name | Growth conditions | Nutrient medium | Incubation |
|---|---|---|---|---|
| *Brevibacterium epidermidis* | ATCC 35514 | Aerobic | Mueller-Hinton agar | 18 h at 36° C. |
| *Corynebacterium xerosis* | ATCC 7711 | Aerobic | Mueller-Hinton agar | 18 h at 36° C. |
| *Propionibacterium acnes* | ATCC 11829 | Anaerobic | Wilkins-Chalgren agar | 72 h at 30° C. |
| *Staphylococus epidermidis* | ATCC 12228 | Aerobic | Mueller-Hinton agar | 18 h at 36° C. |
| *Malassezia furfur* | DSM 6171 | Aerobic | Mueller-Hinton agar + 3% Tween 80 | 72 h at 30° C. |
| *Trichophyton mentagrophytes* | CBS 26379 | Aerobic | Mueller-Hinton agar | 72 h at 30° C. |
| *Epidermophyton Floccosum* | CBS 55384 | Aerobic | Mueller-Hinton agar | 18 h at 36° C. |

MIC Values for 1,2-hexanediol, 1,2-octanediol and a Mixture of the Two Diols in a C6/C8 ratio=2:1

The MIC values for 1,2-hexanediol, 1,2-octanediol and for a mixture of the two diols in a mass ratio of 2 parts of hexanediol to 1 part of octanediol were determined in accordance with the general test conditions described (cf. Table 7).

addition to its excellent activity as a preservative (cf. Example 1) can also preferentially be used for controlling body odour (SI *Staphylococcus epidermidis:* 0.55; SI *Corynebacterium xerosis:* 0.66; SI *Brevibacterium epidermidis:* 0.83), for controlling acne (SI *Propionibacterium acnes:* 0.25) and for controlling the skin and nail mycoses caused by *Trichophyton*

TABLE 7

MIC values [ppm] for 1,2-hexanediol, 1,2-octanediol and for a C6/C8 diol mixture (2:1)
Determination of the Synergy Indices (SI) in accordance with the Kull et al[1,2] equation

| Microorganism | Strain No. | MIC C6 | MIC C8 | MIC C6/C8 2:1 | SI: C6/C8; 2:1 |
|---|---|---|---|---|---|
| *Staphylococcus epidermidis* | ATCC 12228 | 25000 | 12500 | 6250 | 0.55 |
| *Corynebacterium xerosis* | ATCC 7711 | 12500 | 6250 | 6250 | 0.66 |
| *Brevibacterium epidermidis* | ATCC 35514 | 25000 | 3125 | 6250 | 0.83 |
| *Propionibacterium acnes* | ATCC 11829 | 25000 | 6250 | 3125 | 0.25 |
| *Malassezia furfur* | DSM 6171 | 12500 | 50000 | 50000 | 2.97 |
| *Trichophyton mentagrophytes* | CBS 26379 | 6300 | 1562 | 1562 | 0.49 |
| *Epidermophyton floccosum* | CBS 55384 | 6250 | 3125 | 1562 | 0.32 |

[1]F. C. Kull et al.; Applied Microbiology 9; p. 538–541 (1961)
[2]D. C. Steinberg; Cosmetics & Toiletries 115 (11); p. 59–62 (2000)

and *Epidermophyton* species (SI *Trichophyton mentagrophytes:* 0.49; SI *Epidermophyton floccosum:* 0.32). On the other hand, in the case of *Malassezia furfur* it was not possible to demonstrate a synergistic effect for the 1,2-hexanediol/1,2-octanediol mixture (SI *Malassezia furfur:* 2.97, i.e. antagonistic effect).

EXAMPLE 3

Testing of Adequate Preservation by Mixtures of (a) Synergistic Mixtures of 1,2-alkanediols with (b) Further Preservatives Testing for adequate preservation by mixtures of (a) synergistic mixtures of 1,2-alkanediols with (b) further preservatives was likewise carried out in accordance with the European pharmacopoeia. The test procedure is described in detail in Example 1.

Test Germs:

The following microorganism strains were used for the tests for adequate preservation:

A: *Escherichia coli* ATCC 8739

B: *Pseudomonas aeruginosa* ATCC 9027

C: *Staphylococcus aureus* ATCC 6538

D: *Candida albicans* ATCC 10231

E: *Aspergillus niger* ATCC 16404

The initial germ count (CFU/g; "0" value") was in the range of 280,000 to 320,000 in the various test series.

Formulation

For the tests for adequate preservation the potentially synergistic combinations of active compounds taken into consideration, consisting of (a) the 1,2-diol mixtures according to the invention and (b) further preservatives, were incorporated in emulsions in a defined amount. For comparison purposes the corresponding 1,2-diol mixtures according to the invention and the further preservatives tested were incorporated separately into the same O/W emulsions.

Table 8 shows, by way of example, the formulation for a mixture according to the invention consisting of 0.05% Euxyl K400 (mixture of 1,2-dibromo-2,4-dicyanobutane (20%) and 2-phenoxyethanol (80%)), 0.25% 1,2-hexanediol and 0.25% 1,2-octanediol. The variation in the total concentration of 1,2-diol mixture and additional preservative Euxyl K400 in the O/W emulsions was compensated for by increasing or lowering the water content, so that otherwise identical formulations always comprised 100 parts by weight in total.

TABLE 8

Illustrative formulations for O/W emulsion containing A) 0.1% Euxyl K 400, B) 1% of a 1,2-diol mixture made up of 0.5% 1,2-hexanediol and 0.5% 1,2-octanediol and C) a combination of active compounds consisting of 0.05% Euxyl K 400, 0.25% 1,2-hexanediol and 0.25% 1,2-octanediol.

| Raw material (Tradename indicated in some cases) | Manufacturer | A 0.1% Euxyl K400 | % (m/m) B 0.5% hexanediol 0.5% octanediol | C 0.05% Euxyl K400 0.25% hexanediol 0.25% octanediol |
|---|---|---|---|---|
| Octanediol | DRAGOCO | 0 | 0.5 | 0.25 |
| Hexanediol | DRAGOCO | 0 | 0.5 | 0.25 |
| Euxyl K 400 | Schülke/Mayr | 0.1 | 0 | 0.05 |
| K sorbate | Ringe + Kuhlmann | 0 | 0 | 0 |
| Phenoxyethanol | | 0 | 0 | 0 |
| Paraben mixture | | 0 | 0 | 0 |
| Water, low germ | | 79.25 | 78.35 | 78.75 |
| Citric acid, 10% | | 0.15 | 0.15 | 0.2 |
| Dragophos S | DRAGOCO | 2 | 2 | 2 |
| PCL Liquid | DRAGOCO | 3 | 3 | 3 |
| Isodragol | DRAGOCO | 7 | 7 | 7 |
| Lanette 18 | COGNIS | 4.5 | 4.5 | 4.5 |
| Dracorin GMS | 2/008474 | 2 | 2 | 2 |
| Dow Corning 200 fl. | Dow Corning | 2 | 2 | 2 |
| Total | | 100 | 100 | 100 |

Result:

The results of the preservative loading tests for the combinations of active compounds tested, consisting of a synergistic mixture of 1,2-alkanediols according to the invention and a further preservative, are given in Tables 9 and 10 for the system 1,2-hexanediol/1,2-octanediol//Euxyl K400 by way of example. Surprisingly, it was found that not only 1,2-diol mixtures themselves but also combinations of 1,2-diol mixtures with further preservatives are able to achieve a significant synergistic intensification of activity compared with the individual substances metered in the same concentration. In the example mentioned, this is shown in particular in the residual germ counts for *Aspergillus niger* remaining after 28 days. As can be seen from Table 9, in the case of *Aspergillus niger*, a germ that is particularly problematical with regard to the preservation of industrial products, it was possible to reduce the germ count to 2,800 within 28 days by using formulation C. On the other hand, the diol mixture according to formulation B (1,2-hexanediol+1,2-octanediol; mass ratio 1:1) tested in a dosage of 1% and formulation A (containing Euxyl K400), which was also tested in a concentration of 0.1% for comparison purposes, did not enable such a significant reduction in the number of colony forming units (CFU)

in the case of *Aspergillus niger*. The test series (Tab. 9) thus shows, by way of example, that mixtures of active compounds consisting of (a) at least two different members of the group that consists of 1,2-pentanediol, 1,2-hexanediol, 1,2-octanediol and 1,2-decanediol and (b) a further preservative can possess a synergistic, further improved action.

TABLE 9

Testing for adequate preservation for a combination of active compounds consisting of a synergistically active diol mixture according to the invention (1,2-hexanediol and 1,2-octanediol) and a further preservative Euxyl K400; [CFU/ml]

| Days | Escherichia Coli | Pseudomonas aeruginosa | Staphylococcus Aureus | Candida albicans | Aspergillus niger |
|---|---|---|---|---|---|
| 1. O/W emulsion with formulation A (0.1% Euxyl K400) | | | | | |
| 0 | 300,000 | 320,000 | 310,000 | 310,000 | 280,000 |
| 1 | 200 | 0 | 0 | <100 | 220,000 |
| 2 | <100 | 0 | 0 | <100 | 140,000 |
| 4 | 0 | 0 | 0 | 0 | 120,000 |
| 7 | 0 | 0 | 0 | 0 | 200,000 |
| 14 | 0 | 0 | 0 | 0 | 160,000 |
| 28 | 0 | 0 | 0 | 0 | 32,000 |
| 2. O/W emulsion with formulation B (0.5% hexanediol + 0.5% octanediol) | | | | | |
| 0 | 300,000 | 320,000 | 310,000 | 310,000 | 280,000 |
| 1 | 0 | 0 | 0 | 3,200 | 180,000 |
| 2 | 0 | 0 | 0 | 200 | 160,000 |
| 4 | 0 | 0 | 0 | 100 | 140,000 |
| 7 | 0 | 0 | 0 | 0 | 180,000 |
| 14 | 0 | 0 | 0 | 0 | 120,000 |
| 28 | 0 | 0 | 0 | 0 | 60,000 |
| 3. O/W emulsion with formulation C (0.25% hexanediol + 0.25% Octanediol + 0.05% Euxyl K 400) | | | | | |
| 0 | 300,000 | 320,000 | 310,000 | 310,000 | 280,000 |
| 1 | <100 | <100 | <100 | <100 | 20,000 |
| 2 | 0 | 0 | 0 | 0 | 12,000 |
| 4 | 0 | 0 | 0 | 0 | 10,000 |
| 7 | 0 | 0 | 0 | 0 | 8,000 |
| 14 | 0 | 0 | 0 | 0 | 8,000 |
| 28 | 0 | 0 | 0 | 0 | 2,800 |

Based on the available data, the synergistic intensification of the activity of the combination of active compounds consisting of (a) a synergistically active mixture of 1,2-alkanediols according to the invention (for example 1,2-hexanediol and 1,2-octanediol) and (b) a further preservative (for example Euxyl K400) can also be demonstrated on the basis of the Kull equation (F. C. Kull et al.; Applied Microbiology Vol. 9, p. 538-541 (1961); David C. Steinberg; Cosmetics & Toiletries Vol. 115 (No. 11), p. 59-62; November 2000; see also Table 10 for the method of calculation). The Kull equation enables the pure substances and the active compound mixtures prepared therefrom to be compared in respect of their antimicrobial activity. With this equation the so-called synergy index (SI), which is a measure for a synergistic activity, but also for a possible antagonistic activity, of a mixture having an antimicrobial action, is determined. A synergistic effect is evident if the SI value determined is less than 1. On the other hand, if an SI of precisely 1 is calculated, there is a pure additive effect of two substances having an antimicrobial action. In the case of an SI value greater than 1, on the other hand, there is a (frequently undesired) antagonistic effect.

By way of example the calculation of the SI value for the treatment of *Aspergillus niger* with a mixture consisting of 1,2-hexanediol, 1,2-octanediol and Euxyl K400 (formulation C) after an incubation phase of 28 days is shown below. The calculated SI of 0.066 clearly shows that the mixture consisting of 1,2-hexanediol, 1,2-octanediol and Euxyl K400 is a highly synergistic combination of active compounds.

TABLE 10

Calculation of the synergy index (SI) of a 1,2-hexanediol/1,2-octanediol/Euxyl K400 mixture (Formulation C) consisting of equal parts of the comparison 1,2-alkanediol mixture (Formulation A) and of the comparison solution Euxyl K400 (Formulation B) (mass ratio 1:1.; dosage in O/W emulsion: test germ: *Aspergillus niger*)

| | A<br>1,2-hexanediol<br>0.5% + 1,2-octanediol<br>0.5% | B<br>Euxyl K400<br>0.1% | C<br>1,2-hexanediol<br>(0.25%) + 1,2-octanediol (0.25) +<br>EuxylK400<br>(0.05%); |
|---|---|---|---|
| *Aspergillus niger*: 28 days [CFU/ml] | 60000 | 32000 | 2800 |
| Kull equation: SI = C × D/A + C × E/B | | | |
| A: Germ count for substance A | 60000 | | |
| B: Germ count for substance B | 32000 | | |
| C: Germ count for mixture of A + B | 2800 | | |
| D: Amount of A in C | 0.5 | | |
| E: Amount of B in C | 0.5 | | |
| SI: Synergy Index | 0.066 | | |

Literature: Synergy Index:

D. C. Steinberg; Cosmetics & Toiletries 115 (11); p. 59-62 (2000)

F. C. Kull et al.; Applied Microbiology 9; p. 538-541 (1961)

TABLE 3

Testing for adequate preservation for 1,2-diols and 1,2 [lacuna] diol mixtures [CFU/ml]

| | SL | | | | | | | |
|---|---|---|---|---|---|---|---|---|
| | 231001 PE3 | 231001 HE3 | 231001 OC3 | 010801 DE3 | 050601 DEH | 231001 HE/OC | 231001 HE/OC/PE | 231001 HE/OC/DE |
| | Code | | | | | | | |
| | PE3 Pentanediol 3% | HE3 Hexanediol 3% | OC3 Octanediol 3% | DE 3 Decanediol 3% | PE2DE1 Pentanediol 2% Decanediol 1% | HE2/OC1 Hexanediol 2% Octanediol 1% | PE1HE1OC1 Pentanediol 1% Hexanediol 1% Octanediol 1% | HE1OC1DE1 Hexanediol 1% Octanediol 1% Decanediol 1% |
| *E. coli* | | | | | | | | |
| 0'-count | 300,000 | 300,000 | 300,000 | 350,00 | 290,000 | 300,000 | 300,000 | 300,000 |
| 24 h | 300,000 | <100 | 0 | 0 | 0 | 0 | 0 | 0 |
| 48 h | 145,000 | <100 | 0 | 0 | 0 | 0 | 0 | 0 |
| 4 d | 100,000 | 0 | 0 | 0 | 0 | 0 | 0 | 0 |
| 7 d | 40,000 | 0 | 0 | 0 | 0 | 0 | 0 | 0 |
| 14 d | 500 | 0 | 0 | 0 | 0 | 0 | 0 | 0 |
| 28 d | 0 | 0 | 0 | 0 | 0 | 0 | 0 | 0 |
| *Ps. aeruginosa* | | | | | | | | |
| 0'-count | 290,000 | 290,000 | 290,000 | 360,000 | 270,000 | 290,000 | 290,000 | 290,000 |
| 24 h | 145,000 | <100 | 0 | 2,600 | 0 | 0 | 0 | 0 |
| 48 h | 12,000 | <100 | 0 | 1.0 mill. | 0 | 0 | 0 | 0 |
| 4 d | 0 | 0 | 0 | 17.2 mill. | 0 | 0 | 0 | 0 |
| 7 d | 0 | 0 | 0 | 20.0 mill | 0 | 0 | 0 | 0 |
| 14 d | 0 | 0 | 0 | 15.0 mill | 0 | 0 | 0 | 0 |
| 28 d | 0 | 0 | 0 | 11.8 mill | 0 | 0 | 0 | 0 |
| *Staph. aureus* | | | | | | | | |
| 0'-count | 240,000 | 240,000 | 240,000 | 350,000 | 250,000 | 240,000 | 240,000 | 240,000 |
| 24 h | 100,000 | <100 | 0 | 3,200 | 100 | 0 | 0 | 0 |
| 48 h | 12,000 | <100 | 0 | 0 | 0 | 0 | 0 | 0 |
| 7 d | 0 | 0 | 0 | 0 | 0 | 0 | 0 | 0 |
| 14 d | 0 | 0 | 0 | 0 | 0 | 0 | 0 | 0 |
| 28 d | 0 | 0 | 0 | 0 | 0 | 0 | 0 | 0 |
| *C. albicans* | | | | | | | | |
| 0'-count | 250,000 | 250,000 | 250,000 | 320,000 | 300,000 | 250,000 | 250,000 | 250,000 |
| 24 h | 245,000 | 120,000 | 3,200 | 3,500 | 54,000 | 1,700 | 1,800 | 12,000 |
| 48 h | 73,000 | 5,600 | <100 | 0 | 400 | 0 | 0 | <100 |
| 4 d | 28,000 | 0 | 0 | 0 | 0 | 0 | 0 | 0 |
| 7 d | 23,000 | 0 | 0 | 0 | 0 | 0 | 0 | 0 |
| 14 d | <100 | 0 | 0 | 0 | 0 | 0 | 0 | 0 |
| 28 d | 0 | 0 | 0 | 0 | 0 | 0 | 0 | 0 |
| *A. niger* | | | | | | | | |
| 0'-count | 260,000 | 260,000 | 260,000 | 250,000 | 250,000 | 260,000 | 260,000 | 260,000 |
| 24 h | 180,000 | 120,000 | 55,000 | 73,000 | 180,000 | 12,000 | 30,000 | 180,000 |
| 48 h | 180,000 | 120,000 | 6,000 | 160,000 | 82,000 | 10,000 | 18,000 | 160,000 |
| 4 d | 180,000 | 120,000 | 6,000 | 100,000 | 64,000 | 8,000 | 16,000 | 140,000 |
| 7 d | 140,000 | 80,000 | 1,100 | 100,000 | 20,000 | 600 | 16,000 | 20,000 |
| 14 d | 140,000 | 28,000 | 1,000 | 73,000 | 12,000 | 300 | 600 | 6,000 |
| 28 d | 100,000 | 800 | 100 | 73,000 | 5,200 | 0 | 0 | 1,000 |

We claim:

1. An antimicrobial composition, comprising an antimicrobial effective amount of a mixture of 1,2-alkanediols consisting of two or more straight chain 1,2-alkanediols having chain lengths that (i) are different and (ii) in each case are in the range of 5 to 10 C atoms, wherein said mixture of 1,2-alkanediols exhibits an antimicrobial effect characterized by a Kull value of less than 1.

2. The antimicrobial composition according to claim 1, wherein the proportions of the said diols in the mixture are set such that a Kull value of 0.83 or less for the antimicrobial effect exhibited by said mixture of 1,2-alkanediols results.

3. The antimicrobial composition according to claim 1, wherein the mixture contains 1,2-hexanediol and one, two or three further straight-chain 1,2-alkanediols, the chain length of which in each case is in the range of 5 to 10 C atoms.

4. An antimicrobial composition comprising an antimicrobial effective amount of a mixture of 1,2-alkanediols consisting of at least one of:

(a) 1,2-hexanediol and 1,2-octanediol,
(b) 1,2-hexanediol and 1,2-decanediol,
(c) 1,2-pentanediol, 1,2-hexanediol and 1,2-octanediol,
(d) 1,2-hexanediol, 1,2-octanediol and 1,2-decanediol and
(e) 1,2-pentanediol, 1,2-hexanediol and 1,2-decanediol as antimicrobial active compounds, the proportions of the said diols in the mixture of 1,2-alkanediols being set such that a Kull value of less than 1.0 for the antimicrobial effect exhibited by said mixture of 1,2-alkanediols results.

5. The antimicrobial composition according to claim 1, wherein the proportion of each individual diol is in the range of 20 to 80% (m/m) based on the total mass of the mixture of the diols.

6. An antimicrobial composition comprising an antimicrobial effective amount of a mixture of 1,2-alkanediols consisting of two or more straight chain 1,2-alkanediols having chain lengths of which (i) are different and (ii) are in the range of 5 to 10 C atoms, wherein the proportions of said diols in the mixture of 1,2-alkanediols are set such that a Kull value of less than 1.0 for the antimicrobial effect exhibited by said mixture of 1,2-alkanediols results for at least one of:
(a) a cosmetic treatment of microorganisms causing body odour,
(b) a cosmetic treatment of microorganisms causing acne,
(c) a cosmetic treatment of microorganisms causing mycoses,
(d) a treatment of microorganisms on or in inanimate material and
(e) preservation of a perishable product.

7. An antimicrobially active pharmaceutical composition consisting of an antimicrobial effective amount of a mixture of 1,2-alkanediols consisting of two or more straight chain 1,2-alkanediols having chain lengths of which (i) are different and (ii) are in the range of 5 to 10 C atoms, wherein the proportions of the said diols in the mixture of 1,2-alkanediols are such that said mixture of 1,2 alkanediols exhibits an antimicrobial effect characterized by a Kull value of less than 1.0.

8. An antimicrobial composition according to claim 1, further comprising an antimicrobial active compound in an amount at which an antimicrobial action of a mixture of said antimicrobial active compound and said mixture of 1,2-alkanediols is synergistically intensified, the further antimicrobial active compound not being a straight-chain 1,2-alkanediol.

9. An antimicrobial composition, comprising:
(a) as antimicrobial active compound, a mixture of two, three or more straight-chain 1,2-alkanediols, the chain lengths of which (i) are different and (ii) in each case are in the range of 5 to 10 C atoms, and
(b) an excipient compatible with the said mixture, wherein the proportions of the said diols in the mixture are set such that a Kull value of less than 1.0 for the antimicrobial effect exhibited by said mixture of 1,2-alkanediols results.

10. An antimicrobial composition, comprising
(a) an antimicrobial effective amount of a mixture of two, three or more straight-chain 1,2-alkanediols, the chain lengths of which (i) are different and (ii) in each case are in the range of 5 to 10 C atoms, and
(b) a preservative other than straight-chain 1,2-alkanediols, wherein the proportions of the said diols in the mixture are set such that a Kull value of less than 1.0 for the antimicrobial effect exhibited by said mixture of 1,2-alkanediols results.

11. An antimicrobial composition as in claim 10, wherein said preservative (b) is selected from the group consisting of benzoic acid and the esters and salts thereof, propionic acid and salts thereof, salicylic acid and salts thereof, 2,4-hexanoic acid and salts thereof, formaldehyde and paraformaldehyde, 2-hydroxybiphenyl ether and salts thereof, 2-zincsulphidopyridine-N-oxide, inorganic sulphites and bisulphites, sodium iodate, chlorobutanolum, 4-ethylmercury-(II)-5-amino-1,3-bis(2-hydroxy)benzoic acid and salts and esters thereof, dehydracetic acid, formic acid, 1,6-bis(4-amidino-2-bromophenoxy)-n-hexane and salts thereof, the sodium salt of ethylmercury-(II)-thiosalicylic acid, phenylmercury and salts thereof, 10-undecylenic acid and salts thereof, 5-amino-1,3-bis(2-ethylhexyl)-5-methyl-hexahydropyrimidine, 5-bromo-5-nitro-1,3-dioxane, 2-bromo-2-nitro-1,3-propanediol, 2,4-dichlorobenzyl alcohol, N-(4-chlorophenyl)-N'-(3,4-dichlorophenyl)-urea, 4-chloro-m-cresol, 2,4,4'-trichloro-2'-hydroxy-diphenyl ether, 4-chloro-3,5-dimethylphenol, 1,1'-methylene-bis(3-(1-hydroxymethyl-2,4-dioximidazolidin-5-yl)urea), poly-(hexamethylene diguanide) hydrochloride, 2-phenoxyethanol, hexamethylentetramine, 1-(3-chloroalyl)-3,5,7-triaza-1-azoniaadamantane chloride, 1(4-chlorphenoxy)-1(1H-imidazol-1-yl)-3,3-dimethyl-2-butanone, 1,3-bis-(hydroxy-methyl)-5,5-dimethyl-2,4-imidazolidinedione, benzyl alcohol, octopirox, 1,2-dibromo-2,4-dicyanobutane, 2,2'-methylene-bis(6-bromo-4-chloro-phenol), bromo-chlorophene, mixture of 5-chloro-2-methyl-3(2H) isothiazolinone and 2-methyl-3(2H)isothiazolinone with magnesium chloride and magnesium nitrate, 2-benzyl-4-chlorophenol, 2-chloracetamide, chlorhexidine, chlorhexidine acetate, chlorhexidine gluconate, chlorhexidine hydrochloride, 1-phenoxy-propan-2-ol, N-alkyl($C_{12}$-$C_{22}$) trimethyl-ammonium bromide and chloride, 4,4-dimethyl-1,3-oxazolidine, N-hydroxymethyl-N-(1,3-di (hydroxymethyl)-2,5-dioxoimidazolidin-4-yl)-N'-hydroxymethyl urea, 1,6-bis(4-amidino-phenoxy)-n-hexane and salts thereof, glutaraldehyde 5-ethyl-1-aza-3,7-dioxabicyclo (3.3.0)octane, 3-(4-chlorphenoxy)-1,2-propanediol, hyamine, alkyl-($C_8$-$C_{18}$)-dimethyl-benzylammonium chloride, alkyl-($C_8$-$C_{18}$)-dimethyl-benzyl ammonium bromide, alkyl-($C_8$-$C_{18}$)-dimethyl-benzyl ammonium saccharinate, benzylbemiformal, 3-iodo-2-propinylbutyl carbamate, sodium hydroxymethyl-aminoacetate or sodium hydroxymethyl-aminoacetate.

12. An antimicrobial composition as in claim 11, wherein said preservative (b) is 1,2-dibromo-2,4-dicyanobutane.

13. An antimicrobial composition as in claim 11, wherein said preservative (b) is 2-phenoxyethanol.

14. An antimicrobial composition as in claim 10, wherein said preservative (b) is 3-iodo-2-propinyl-butyl carbamate.

15. An antimicrobial composition as in claim 11, wherein said mixture (a) comprises 1,2-hexanediol or 1,2-octanediol.

16. An antimicrobial composition as in claim 10, wherein said mixture of straight-chain 1,2-alkanediols comprises 1,2-hexanediol and 1,2-octanediol.

17. An antimicrobial composition as in claim 10, further comprising a preservative.

18. An antimicrobial composition as in claim 17, wherein said preservative is 3-iodo-2-propinyl-butyl carbamate.

19. An antimicrobial composition as in claim 4, wherein said 1,2-hexanediol and 1,2-octanediol are present in a ratio of 1:1.

20. An antimicrobial composition as in claim 4, wherein said 1,2-hexanediol and 1,2-octanediol are present in a ratio of 2:1.

21. The antimicrobial composition of claim 1, wherein said antimicrobial composition comprises said mixture of 1,2-alkanediols in an amount between 0.01 and 30% (m/m) by mass of said antimicrobial composition.

22. The antimicrobial composition of claim 1, wherein said antimicrobial composition comprises said mixture of 1,2-alkanediols in an amount between 0.1 and 5% (m/m) by mass of said antimicrobial composition.

* * * * *